US010802009B2

(12) United States Patent
Zeng et al.

(10) Patent No.: US 10,802,009 B2
(45) Date of Patent: Oct. 13, 2020

(54) NETWORKED ENVIRONMENTAL MONITORING SYSTEM AND METHOD

(71) Applicants: Ning Zeng, Silver Spring, MD (US); Cory Martin, Washington, DC (US)

(72) Inventors: Ning Zeng, Silver Spring, MD (US); Cory Martin, Washington, DC (US)

(*) Notice: Subject to any disclaimer, the term of this patent is extended or adjusted under 35 U.S.C. 154(b) by 265 days.

(21) Appl. No.: 15/832,745

(22) Filed: Dec. 5, 2017

(65) Prior Publication Data

US 2018/0156766 A1    Jun. 7, 2018

Related U.S. Application Data

(60) Provisional application No. 62/430,384, filed on Dec. 6, 2016.

(51) Int. Cl.
*G01N 33/00* (2006.01)
(52) U.S. Cl.
CPC ....... *G01N 33/004* (2013.01); *G01N 33/0006* (2013.01); *Y02A 50/241* (2018.01)
(58) Field of Classification Search
CPC .................................................. G01N 33/004
See application file for complete search history.

(56) References Cited

U.S. PATENT DOCUMENTS

| 4,678,914 A * | 7/1987 | Melrose ............. G01N 21/3518 250/339.03 |
| 10,054,534 B1 * | 8/2018 | Nourbakhsh .......... G01N 15/06 |
| 2018/0080890 A1 * | 3/2018 | Potyrailo ................. H04Q 9/00 |

FOREIGN PATENT DOCUMENTS

CN         105181898 A    12/2015

OTHER PUBLICATIONS

International Search Report and Written Opinion dated Jan. 30, 2018 in PCT/CN2017/114638.

* cited by examiner

*Primary Examiner* — Hyun D Park
(74) *Attorney, Agent, or Firm* — Syncoda LLC; Feng Ma

(57) ABSTRACT

A system and method for monitoring environment employ a dense network of low-cost sensor nodes. The method includes obtaining environmental information by combining a plurality of observations; wherein the plurality of observations are made with in-situ or remote sensors; wherein the sensors are of different degrees of accuracy in a way to complement each other, and of different cost, and wherein the low-cost sensors form a high-density network comprising a plurality of distributed sensors. The system can monitor gas concentrations over urban areas, industrial, forest, farm, wetland, power plants and other types of surfaces.

14 Claims, 15 Drawing Sheets

NETWORKED ENVIRONMENTAL MONITORING SYSTEM AND METHOD

CROSS-REFERENCE TO RELATED APPLICATIONS

The present application claims priority to U.S. Provisional Patent Application No. 62/430,384 filed on Dec. 6, 2016, the disclosure of which is hereby incorporated by reference in its entirety.

BACKGROUND

Monitoring of the atmospheric environment includes measuring the concentrations of air pollutants such as ozone ($O_3$), carbon monoxide (CO), sulfur oxides ($SO_x$), nitrogen oxides ($NO_x$), and particulate matter (PM).

Increasingly, greenhouse gases (GHGs) such as carbon dioxide ($CO_2$), methane ($CH_4$), and Nitrous Oxide ($N_2O$) are being monitored for climate change mitigation strategies such as global carbon treaties and regional carbon initiative and trading schemes (COP15; National Research Council: Verifying Greenhouse Gas Emissions: Methods to Support International Climate Agreements. National Academies Press).

For example, since $CO_2$ measurements started at the Mauna Loa Observatory in the 1950s (Keeling, C. D., Piper, S. C., Bacastow, R. B., Wahlen, M., Whorf, T. P., Heimann, M., and Meijer, H. A.: Atmospheric $CO_2$ and $^{13}CO_2$ exchange with the terrestrial biosphere and oceans from 1978 to 2000: Observations and carbon cycle implications, History of Atmospheric $CO_2$ and Its Effects on Plants, Animals, and Ecosystems, 177, 83-113, 2005), the global mean concentrations of $CO_2$ have steadily risen from pre-industrial levels of approximately 280 parts per million (ppm), to today's level exceeding 400 ppm (GLOBAL-VIEW-CO2, 2013: Cooperative Global Atmospheric Data Integration Project. 2013, updated annually. Multi-laboratory compilation of synchronized and gap-filled atmospheric carbon dioxide records for the period 1979-2012. Compiled by NOAA Global Monitoring Division: Boulder, Colo., U.S.A.).

These observations, both from flask samples, as well as state-of-the-art continuous measurement instruments, have a typical accuracy of ~0.1 ppm. Flasks require observers to collect the samples, and then need to be transported to a lab for analysis, which costs significant amounts of time and money. Towers do not suffer from these continuous costs, but do have some maintenance costs associated with them, in addition to their high initial price of installation. Because of the limitations of both funding and manpower, carbon dioxide and air pollutant observations have been relatively sparse.

SUMMARY

In an aspect, an environment monitoring method is provided, including: obtaining environmental information by combining a plurality of observations; wherein the plurality of observations are made with in-situ or remote sensors; wherein the sensors are of different degrees of accuracy in a way to complement each other, and of different cost, and wherein the low-cost sensors form a high-density network comprising a plurality of distributed sensors. The in-situ or remote sensors can include, for example, ground-based sensors, air-based sensors, space-based sensors, or a combination thereof.

In some embodiments, the method includes obtaining environmental data with a plurality of distributed sensors, wherein the plurality of distributed sensors comprise low-cost and low-accuracy sensors calibrated to achieve a medium-accuracy suitable for environmental monitoring; and assimilating the obtained data together with meteorological information to derive ultra-high-resolution information on the environment.

In another aspect, an environment monitoring system is provided, including: a plurality of distributed sensors configured to obtain environmental data, wherein the plurality of distributed sensors comprise low-cost and low-accuracy sensors calibrated to achieve a medium-accuracy suitable for environmental monitoring; and a processor configured to assimilate the obtained data together with meteorological information to derive ultra-high-resolution information on the environment.

In another aspect, an environmental sensor calibration apparatus is provided, including: a housing; a standard gas source; one or more vents configured to introduce ambient air into the housing; one or more sensors configured to measure ambient temperature, humidity, and air pressure; a processor configured to calibrate raw data from a plurality of low-cost sensors based on the measured temperature, humidity, and air pressure using a regression method.

In another aspect, a non-transitory computer-readable medium having instructions stored thereon for environment monitoring is provided, the instructions including: obtaining environmental data with a plurality of distributed sensors, wherein the plurality of distributed sensors comprise low-cost and low-accuracy sensors calibrated to achieve a medium-accuracy suitable for environmental monitoring; and assimilating the obtained data together with meteorological information to derive ultra-high-resolution information on the environment.

In another aspect, a smartphone-implemented software (e.g., an "App") is provided, including a plurality of instructions to: obtain environmental data from a plurality of distributed sensors, wherein the plurality of distributed sensors comprise low-cost and low-accuracy sensors calibrated to achieve a medium-accuracy suitable for environmental monitoring; assimilate the obtained data together with meteorological information to derive ultra-high-resolution information on the environment; and display the ultra-high-resolution information over a map.

Another aspect involves procedures and algorithms applied to low-accuracy gas sensors for noise reduction, calibration, and environmental variable correction to improve the sensor resolution and accuracy such that they become suitable for ambient concentration gas monitoring. Another aspect involves the development of a device that enables the calibration and correction procedures both on device and through cloud computing using networked devices and modeling. Another aspect involves using data assimilation techniques to combine the measured gas concentrations and meteorological information to derive ultra high-resolution information on pollution sources and sinks.

Other aspects and implementations may become apparent in view of the following drawings and detailed description.

DETAILED DESCRIPTION

Figure 1:
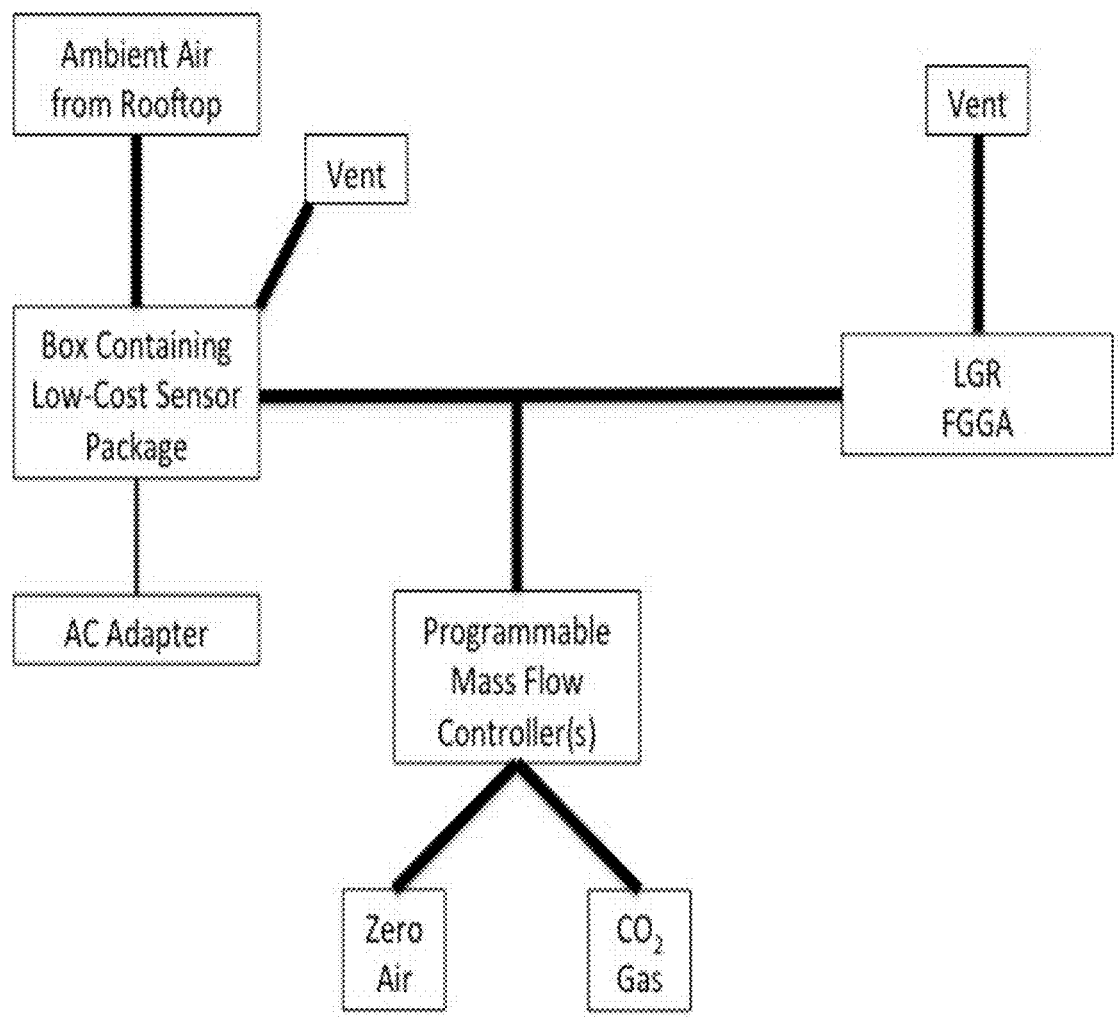
FIG. 1 is a description of a lab calibration setup utilizing both reference gas and ambient air according to some embodiments.

Conventional environmental monitoring networks such as the global $CO_2$ network GLOBALVIEW-CO2 are typically at a low spatial resolution, which can reveal carbon sources and sinks at continental/country scale. Medium-resolution monitoring systems are for regional scale monitoring, high-resolution monitoring systems are for city-scale monitoring, and ultra-high-resolution monitoring systems are for sub-city (e.g., on a scale of a few kilometers or smaller) monitoring.

Recent research efforts have focused more on local observations, and on the use of networks of observing sites that employ instrumented towers similar to those for global monitoring, but instead applied to the urban environment (Briber, Brittain M., Lucy R. Hutyra, Allison L. Dunn, Steve M. Raciti, and J. William Munger. 2013. Variations in atmospheric CO2 mixing ratios across a Boston, Mass. urban to rural gradient. Land 2(3): 304-327; Kort, E., W. Angevine, C. E. Miller, R. Duren (2013), Surface observations for monitoring megacity greenhouse gas emissions: minimum requirements for the Los Angeles Megacity, J. Geophys Res A, 2013, DOI: 10.1002/jgrd.50135; Turnbull, J. C., Sweeney, C., Karion, A., Newberger, T., Lehman, S. J., Tans, P. P., Davis, K. J., Lauvaux, T., Miles, N. L., Richardson, S. J., Cambaliza, M. O., Shepson, P. B., Gurney, K., Patarasuk, R., and Razlivanov, I.: Toward quantification and source sector identification of fossil fuel $CO_2$ emissions from an urban area: Results from the INFLUX experiment, Journal of Geophysical Research-Atmospheres, 120, 292-312, 10.1002/2014jd022555, 2015).

Data from these sparse tower sites are then used to create inversions to estimate the total greenhouse gas flux from the urban area in question. However, due to the cost of these networks being comparable to ones at the global scale, the observation towers are still sited at a relatively low density.

To better constrain the inversion estimates, there is a need for a higher spatial density in the data collected. Air pollution monitoring stations are also generally very few over even the best-monitored major metropolitan areas such as Baltimore-Washington, Beijing, and Paris, where emission sources are known to be highly variable in space and time from traffic patterns, utilities, and point sources (Gurney, K. R., I. Razlivanov, Y. Song, Y. Zhou, B. Benes, and M. Abdul-Massih, 2012: Quantification of Fossil Fuel CO2 Emissions on the Building/Street Scale for a Large U.S. City, Environ. Sci. Technol., 46, 12194-12202, doi:10.1021/es3011282; Hutyra, L., R. Duren, K. R. Gurney, N. Grimm, E. Kort, E. Larson, G. Shrestha (2014), Urbanization and the carbon cycle: Current capabilities and research outlook from the natural sciences perspective, Earth's Future, doi: 10.1002/2014EF000255).

Knowledge of the spatial and temporal patterns of air pollution and greenhouse gases in the immediate environment of individuals and organizations can enhance environmental awareness and facilitate actions to reduce emissions. Systems and methods are disclosed herein, which can contribute to such a goal at affordable costs.

Gas sensors use a variety of mechanisms/materials including electrochemical, metal oxide, and optical approaches. However, the accuracy and stability of most low-cost industrial sensors are generally not sufficient for ambient GHG and air pollution monitoring, and are considered to be low-accuracy sensors.

For $CO_2$ sensors, a low-accuracy sensor can have a measurement accuracy (error) of larger than 10 ppm. A high-accuracy sensor can have a measurement accuracy of smaller than 1 ppm, such as 0.1-0.5 ppm. A medium-accuracy sensor can have an accuracy of about 1-10 ppm, such as 2-5 ppm.

While low-accuracy sensors are useful for industrial applications, environmental monitoring need sensors that can achieve at least a medium accuracy. According to some embodiments disclosed herein, a method and instrumentation technique are provided, which can improve low-accuracy (e.g., low-cost) sensors to be suitable for ambient concentration monitoring in stand-alone mode or networked mode. The methods according to some embodiments disclosed herein can be applied to a variety of air sensors for different gases and air pollutants, and the specifics of the description uses the SenseAir K30 $CO_2$ sensor, which uses non-dispersive infrared (NDIR) light absorption to detect concentration, as an example.

1. Calibration Procedures and Algorithms

Compared to traditional single-site scientific measurements, the large quantity of sensors and high autonomous requirement in one envisioned use of a dense network of such sensors pose a unique set of challenges for calibration (Bergin, Mike; Karoline Johnson; Armistead Russell: Low cost sensors: Field Evaluations and multi-sensor approaches for emissions factors. Presentation at the EPA workshop "EPA Air Sensors 2014: A New Frontier", June, 2014, EPA's Research Triangle Park Campus, NC; Spinelle, L., M. G. Villani, D. Suriano, M. Penza, M. Gerboles and M. Aleixandre, Calibration of a cluster of low-cost sensors for the measurement of air pollution in ambient air, poster presented at the MACPoll Final Conference, delft, 13-14 May 2014).

A variety of calibration methods according to embodiments disclosed herein can be used separately or in combination, some involving a single sensor, some a network of sensors. Some example methods disclosed herein apply to a variety of air sensors for different gases and air pollutants.

The calibration methods can include, for example: (1) lab calibration with compressed reference gases and ambient air prior to field deployment, (2) calibration and correction for environmental variables with continuous ambient air inside a large chamber, (3) periodic retrieval for lab calibration, (4) in-situ zero-drift correction, (5) co-location with standard monitoring stations, and (6) network-enabled calibration. These are discussed in detail below.

1.1 Lab Calibration with Calibration Gas and Continuous Ambient Air

As shown in FIG. 1, the sensors are housed in a container with periodic known gas concentrations traced back to NIST standards (Martin, C. R., N. Zeng, X. Ren, R. R. Dickerson, K. J. Weber, B. N., Turpie. 2016. Performance and Environmental Correction of a Low-Cost NDIR CO2 Sensor. Atmospheric Measurement Techniques, amt-2016-396), and ambient air pumped in during other times. Because of the cost of calibration gas, it is preferable to use it sparingly for the initial calibration with a large quantity of sensors at once.

In an analysis, four K30s were installed in a semi-airtight container in a laboratory. The container was placed inline upstream of a Los Gatos Fast Greenhouse Gas Analyzer (LGR), and the LGR's included pump was used to pull ambient outdoor air from an inlet into the container holding the K30s and into the LGR. Additionally, a Dasibi (Model 5008) calibrator was attached to this system, allowing for two NIST traceable calibration gas standards (ultra pure zero air, as well as a $CO_2/CH_4$ mixture near ambient levels) to be introduced to the sensors and the LGR simultaneously. The temperature was kept relatively constant for the K30s, as the laboratory, located in a classroom building, stays at room temperature through the building's HVAC system, but relative humidity may have varied as outside air was pulled into the sensor container. See, e.g., FIG. 1 for a schematic of the instrument setup.

1.2 Calibration and Correction for Environmental Variables with Continuous Ambient Air Inside a Large Chamber Significant uncertainty of these commercial $CO_2$ sensors is due to variations in the ambient temperature, humidity and air pressure. A cavity ring-down spectroscopy analyzer can achieve exceptionally high precision for the measurement of $CO_2$ by controlling the temperature, humidity and pressure within the measurement chamber, but at a high price. According to some embodiments disclosed herein, these environmental variables can be measured, together with the targeted gases, and calibrated after data collection using a multivariate regression analysis, thereby allowing low-cost, low-accuracy sensors to be employed at improved accuracies after the calibrations.

Figure 2:
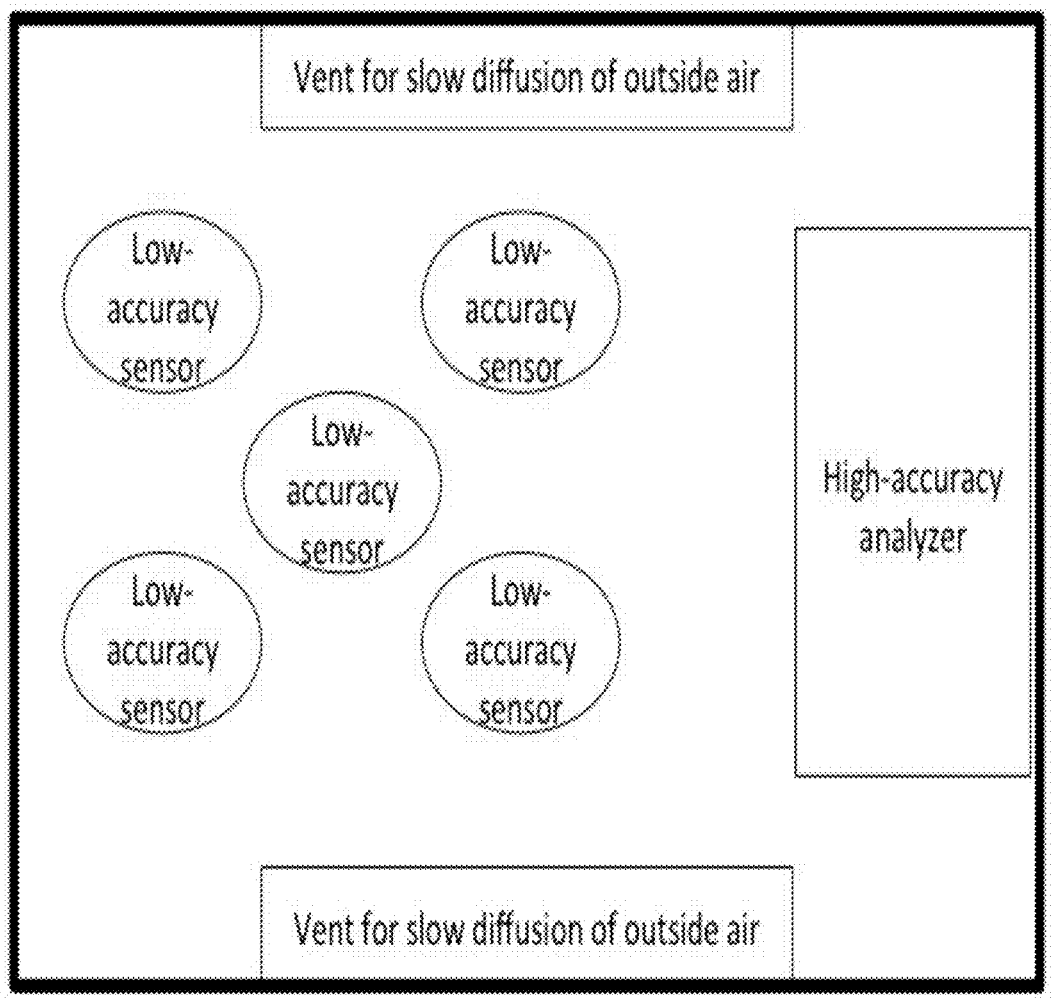
FIG. 2 is a schematic of an example an ambient calibration chamber showing vents to ambient air, and both the high-accuracy analyzer and low-cost sensors sampling air from this chamber concurrently.

As shown in FIG. 2, to evaluate a relatively large number of sensors, an efficient and low-cost calibration procedure with ambient air is disclosed herein, which avoids the use of relatively expensive and complex lab calibration procedure. Additionally, because the calibration is conducted within the range of actual ambient air concentration variation of typically 400-500 ppm of $CO_2$, it may be more accurate for practical use than conventional lab zero/span calibration, for example, a two-point calibration at 0 ppm and 400 ppm, because of likely non-linearity in the response.

In an example, a rooftop observation chamber/room can be used for this ambient calibration procedure. The exchange of air inside the chamber is controlled by changing the degree of 1-2 pipe openings on the walls of the chamber to allow ambient outdoor air to slowly diffuse into the room. A small household box fan in this example is used to ensure that the air is well mixed. The room can be temperature controlled with an HVAC unit, or without air conditioning, and some results shown did not use temperature control. With the exception of daytime heating warming the room more than the outside air, the interior temperature took on a diurnal cycle similar to the outdoor temperature. This ventilation strategy was intentional so that the room then mimics the ambient $CO_2$ concentration of the surrounding atmosphere, and approximates the outdoor temperature and humidity, while protecting instruments from direct sunlight and inclement weather. This provides an advantage over controlled tests in a laboratory setting in that rather than just a multi-point calibration, comparing datasets over ambient concentrations and environmental conditions allows for a realistic evaluation of these instruments in more real world scenarios.

Figure 3:
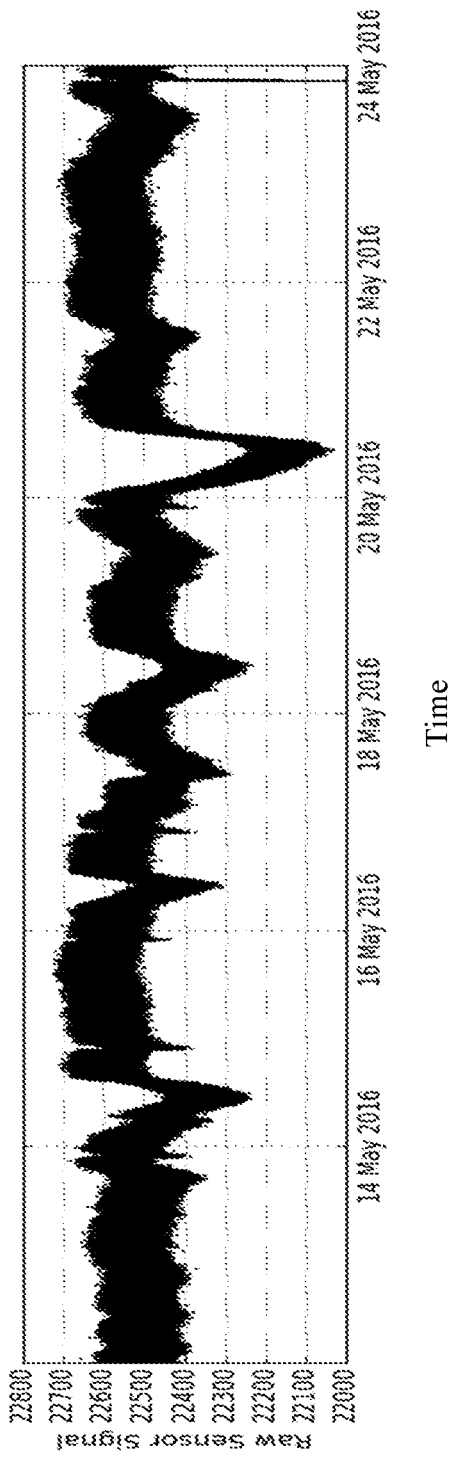
FIG. 3 shows an example of a time series of original raw data from a low-cost $CO_2$ sensor.

In an example, as shown in FIG. 3, raw signal from a sensor for a period of about two weeks in the spring of 2016. The raw K30 data show large noisy variations of more ±30 ppm, in accordance with manufacturer's specified accuracy. Such a precision is too low for most environmental monitoring applications. Here an example 3-step calibration procedure is provided, which can improve the precision to a moderate range of 2-10 ppm.

1.2.1 Time Averaging

The original 2-seconds data are grouped into bins of every tau seconds, with tau varying from 2 to a large value less or equal to the total data duration. For each tau, Allan deviation (see, e.g., Allan, D. W.: STATISTICS OF ATOMIC FREQUENCY STANDARDS, Proceedings of the Institute of Electrical and Electronics Engineers, 54, 221-&, 10.1109/proc.1966.4634, 1966.) is calculated as the standard deviation of the time series comprising the average of the groups. For a K30 $CO_2$ sensor, the minimum standard deviation can be obtained at around tau=200 s.

Figure 4:
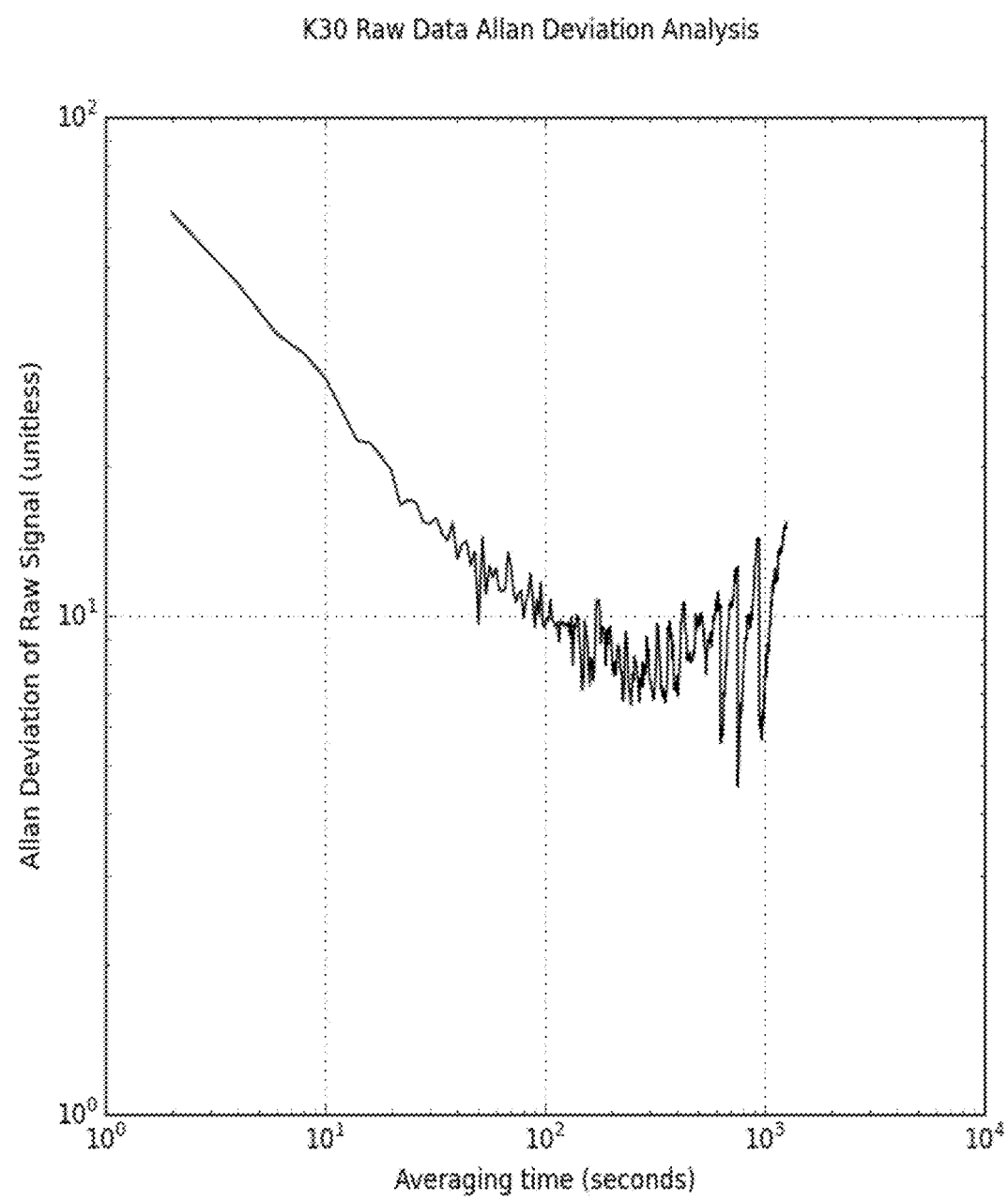
FIG. 4 shows the Allan deviation of the raw data from the same low-cost sensor.

In an example, an averaging interval of 1 minute may be selected where the standard deviation is already an order of magnitude smaller than the noise of individual data points, and is only slightly larger than the minimum value. FIG. 4 shows the Allan deviation for one K30's raw two-second data. The optimum averaging time, when the Allan variance is at a minimum, is around four minutes. This indicates that with averaging periods below four minutes, noise may still exist, and longer than four minutes can result in loss of real signal. For the subsequent analysis, an averaging time of one minute is selected, as the Allan variance is only slightly higher than four minutes, and it is more straightforward to work with data with a frequency of one minute compared to data every four minutes.

1.2.2 Zero/Span Calibration with the Chamber Ambient Measurements.

This can be achieved using a linear regression analysis equation:

$$y = a_0 x_0 + b_0 + \varepsilon_0$$

where y is the K30 measurements, while $x_0$ is the LGR data (assumed to be the true value), $a_0$ and $b_0$ are the regression coefficients and $\varepsilon_0$ is the residual.

The regression coefficients $a_0$ and $b_0$ can be obtained by applying the data to a sufficiently long period of time. They are then used to reconstruct a corrected CO2 value $y^*$:

$$y^* = (y - b_0)/a_0$$

1.2.3 Environmental Correction

Analyzers such as Piccaro and LGR achieve their high accuracy in part by controlling the internal air temperature, pressure, and humidity, which is not feasible in a low-cost system. A method is provided herein where co-measured environmental variables are used to correct the measure value after the previous two steps.

Figure 5:
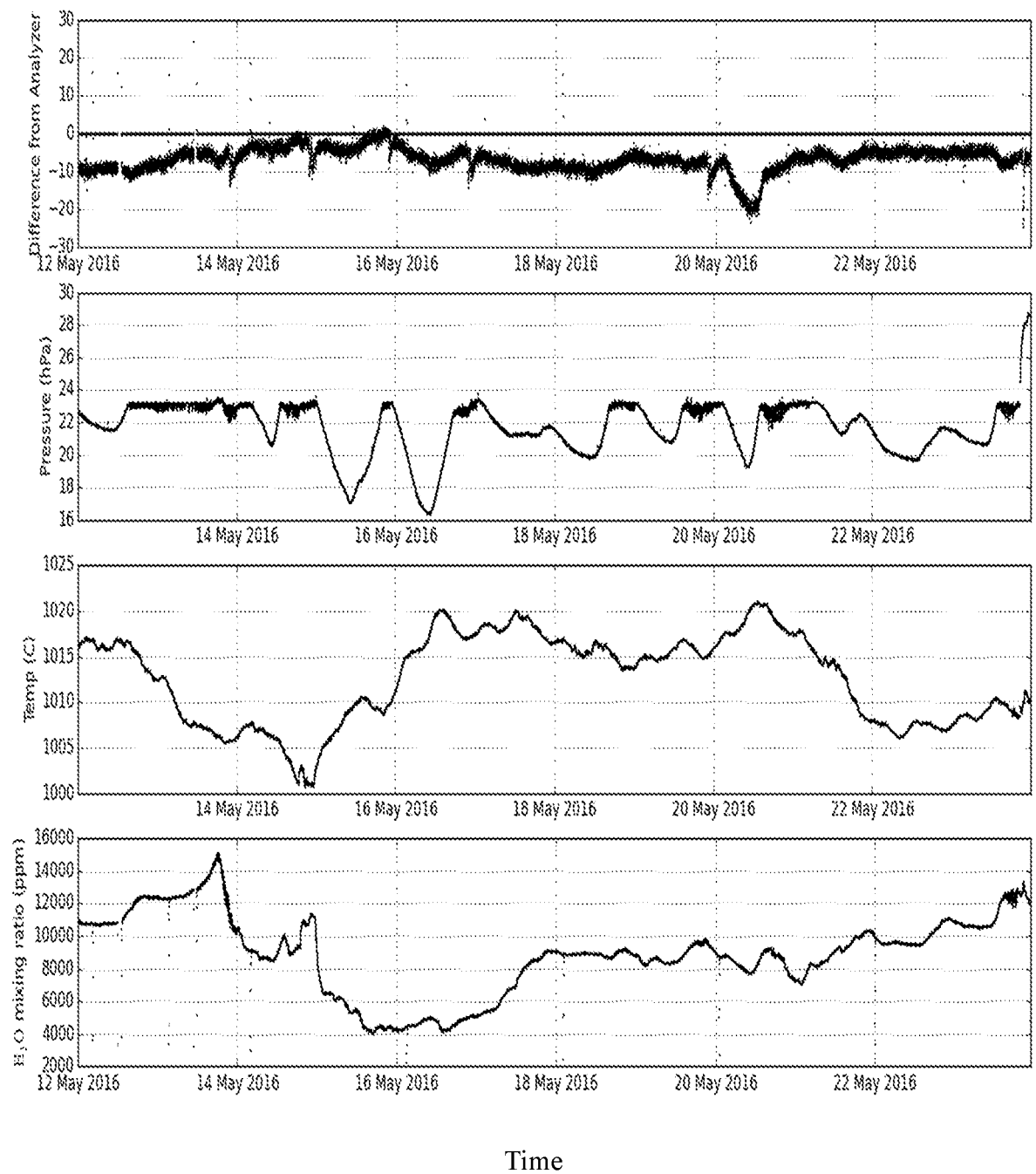
FIG. 5 is plot illustrating a difference between the low-cost sensor data and data obtained from a high-accuracy analyzer, as well as meteorological data.

As shown in FIG. 5, the difference between the LGR and one K30 is shown alongside time series of environmental data from the evaluation chamber. Temperature and pressure are from one of the BMP180 sensors in the room and the water vapor mixing ratio is recorded by the LGR. Just like the difference plot, each of the environmental variables features two distinct wave patterns. There is a diurnal cycle of each variable, as well as synoptic-scale variability attributed to weather systems that occurs on the order of one week.

In an embodiment, an underlying assumption is made that the reported $CO_2$ value y from the low-cost sensor is influenced by the true $CO_2$ value $x_0$ (taken as the value from the high-accuracy LGR instrument in the analysis below), and a number of other factors $x_1, x_2, \ldots, x_n$ such as air pressure, temperature and humidity.

$$y = a_0 x_0 + a_1 x_1 + a_2 x_2 + \ldots a_n x_n + b + \varepsilon_n$$

Two variations of the method can be employed to correct environmental influences on the sensor: (a) successive regression analysis, which has the advantage of identifying the relative contribution from each individual environmental factors; (b) multivariate regression analysis;

1.2.3a Successive Regression Method

Similar to $\varepsilon_0$ in 1.2.2, the residuals at two successive regression steps are related to environmental variables using linear regression successively as:

$$\varepsilon_{n-1} = \varepsilon_n - a_n x_n - b_n$$

where n=1, 3 for each environmental variable pressure p, temperature T, and water vapor q. This linear regression method leads to eight correction coefficients, of the form $a_n$ and $b_n$. These coefficients can then be used in the equation above along with the environmental variables to correct K30 $CO_2$ observations for environmental influences:

$$y^* = \{y - b_0 - (a_1 x_1 b_1) \ldots -(a_n x_n + b_n)\}/a_0.$$

Figure 6:
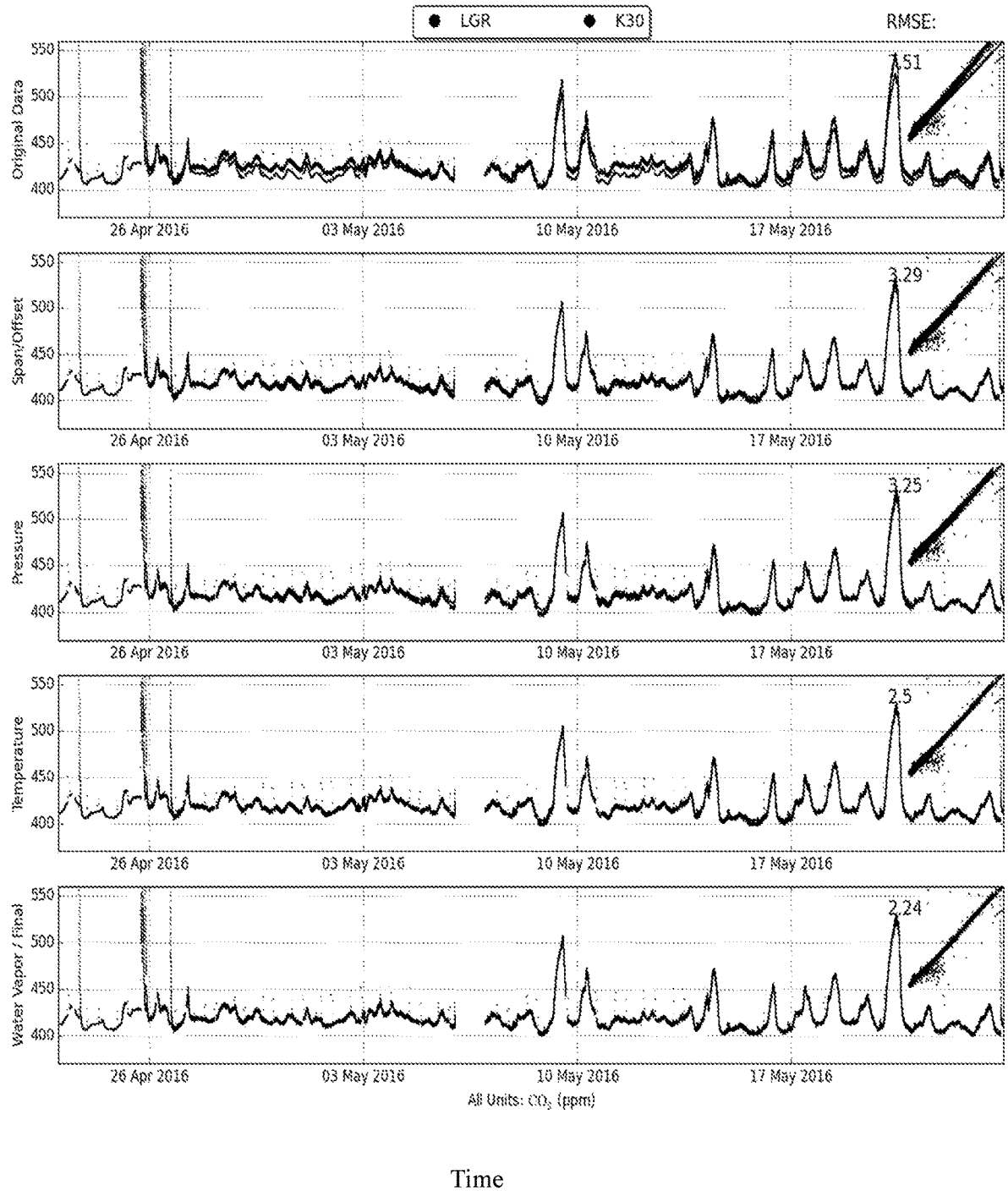
FIG. 6 is a ladder plot of the sensor data at each step of an example iterative correction process.

For the first K30, the initial root mean square error (RMSE) of the data was 18.54 ppm. Using the cumulative univariate regression method, the RMSE decreased after each step. After the initial span and offset regression, it dropped to 3.07 ppm. After correcting for atmospheric pressure, the standard deviation of the difference between the K30 and LGR dropped to 2.71 ppm. Furthermore, including air temperature and water vapor mixing ratio dropped the standard deviation to 2.67 ppm and 2.52 ppm respectively. Therefore, using the successive regression method, the RMSE of the observed difference dropped from 18.54 ppm to 2.52 ppm. See FIG. 6 for the results and scatter plots for each step of the correction for one K30. Another K30, that with the highest observed variability but relatively low offset, had the RMSE decrease from 4.96 ppm to 2.74 ppm. Similar results were observed for each K30 sensor evaluated. A summary can be found in Table 1. The above example analysis corrects environmental variables in the order of pressure, temperature and humidity, but one can alternatively use different order to test the robustness.

1.2.3b Multivariate Linear Regression Method

Alternatively, a multivariate linear regression statistical method can be used to calculate the regression coefficients for each K30 sensor. This results in five correction coefficients $a_n$ and $b_n$ where n represents each independent variable, the dry $CO_2$ from the LGR, pressure P, temperature T, and water vapor mixing ratio q. Like the successive method above, these coefficients can be used similar to the equation above along with the original K30 data, y, and the environmental variables to predict the true $CO_2$ concentration observed.

Figure 7:
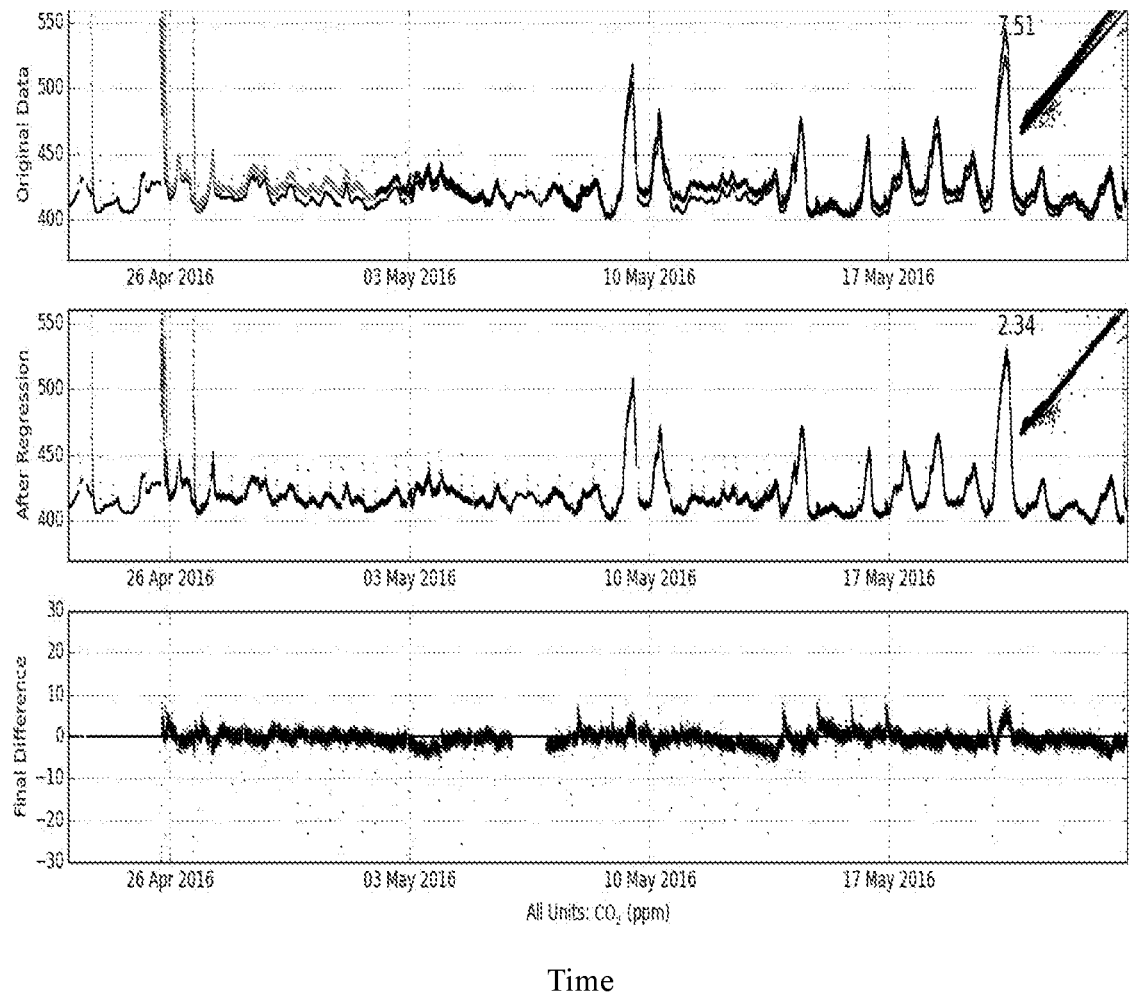
FIG. 7 shows the sensor data before and after an example multivariate correction process.

Using the multivariate regression, the same two K30's differences from the LGR as described in Section 1.2.3a above were reduced to a RMSE of 2.43 ppm and 2.17 ppm, respectively. FIG. 7 shows the results of the multivariate regression for the same K30 as in FIG. 6 as well as the difference between the corrected K30 dataset and the LGR. Like with the univariate method, similar results were observed from each K30 sensor evaluated and a summary can also be found in Table 1.

TABLE 1

|  | Original | Zero/Span | Pressure | Temp | q (final) | Multivariate |
|---|---|---|---|---|---|---|
| K30 # 1 | 18.54 | 3.07 | 2.71 | 2.67 | 2.52 | 2.43 |
| K30 # 2 | 4.96 | 4.16 | 3.96 | 3.55 | 2.74 | 2.17 |
| K30 # 3 | 10.8 | 3.70 | 3.03 | 2.89 | 2.47 | 2.20 |
| K30 # 4 | 3.59 | 3.38 | 2.92 | 2.90 | 2.40 | 2.09 |
| K30 # 5 | 7.14 | 3.00 | 2.70 | 2.42 | 1.97 | 1.68 |
| K30 # 6 | 17.23 | 3.09 | 2.31 | 2.21 | 2.14 | 2.11 |

1.3 Physically Based Pressure Correction

While pressure variations associated with diurnal cycle, synoptic weather and seasonal variations can be corrected by simultaneously measured atmospheric pressure using statistical analysis as discussed above, a more physically based method can be employed to correct pressure influence without co-measurements all the time. This is based on the physical principle that pressure influence on the sensor reading is mostly through changing the quantity of $CO_2$ molecules inside the sensor's internal measurement chamber. Based on the ideal gas law, $$p = nRT$$

where p is pressure, n is mole density of $CO_2$ molecules, R is $CO_2$ mole gas constant, and T is temperature, pressure change leads to a proportional change in mole/number density. Because the optical absorption length of IR light inside the sensor's diffusion chamber is fixed, change in number density leads to proportionally different IR signal at the detector. For example, lower pressure means fewer molecules for the sample optical path length, thus a lower recorded $CO_2$ value, even though the concentration is the same. The procedure leads to a correction of $\Delta y$ to the original value y as:

$$\frac{\Delta y}{y} = \frac{\Delta n}{n} = \frac{\Delta p}{p}$$

Alternatively, an empirical formula between $CO_2$ and pressure can be used such as those derived from the above regression analysis. This procedure can be used for many practical situations, for example, when a lab-calibrated sensor is deployed to a field location at a different elevation. The pressure differences between the two locations are measured for a concurrent period of time. For better results, weather related spatial variations in pressure are corrected using global or regional weather analysis issued by weather forecasting centers, which is then subtracted from the measured pressure values at the two locations to obtain the elevation-only related difference. This difference is then used to correct measured $CO_2$ value. Alternatively, the pressure difference can be approximated based on the elevation difference using a standard meteorological hypsometric equation:

$$Z_2 - Z_1 = \frac{1}{g_0} \int_{p_2}^{p_1} R_d T_v \frac{dp}{p} = \frac{R_d \overline{T_v}}{g_0} \log \frac{p_1}{p_2}$$

where the geopotential height difference between the two locations $Z_2-Z_1$ is related to the pressures $p_1$ and $p_2$, using average virtual temperature $T_v$, gas constant $R_d$ and gravity constant $g_0$.

Another example is continuous measurements at varying height, for example, in the case that the sensor is carried by a balloon, a kite, an airplane, or an unmanned aerial vehicle (UAV). In this case, simultaneously measured pressure change can be used, or derived using height information detected by onboard GPS instrumentation.

1.4 In-Situ Zero-Drift Correction

Figure 8:
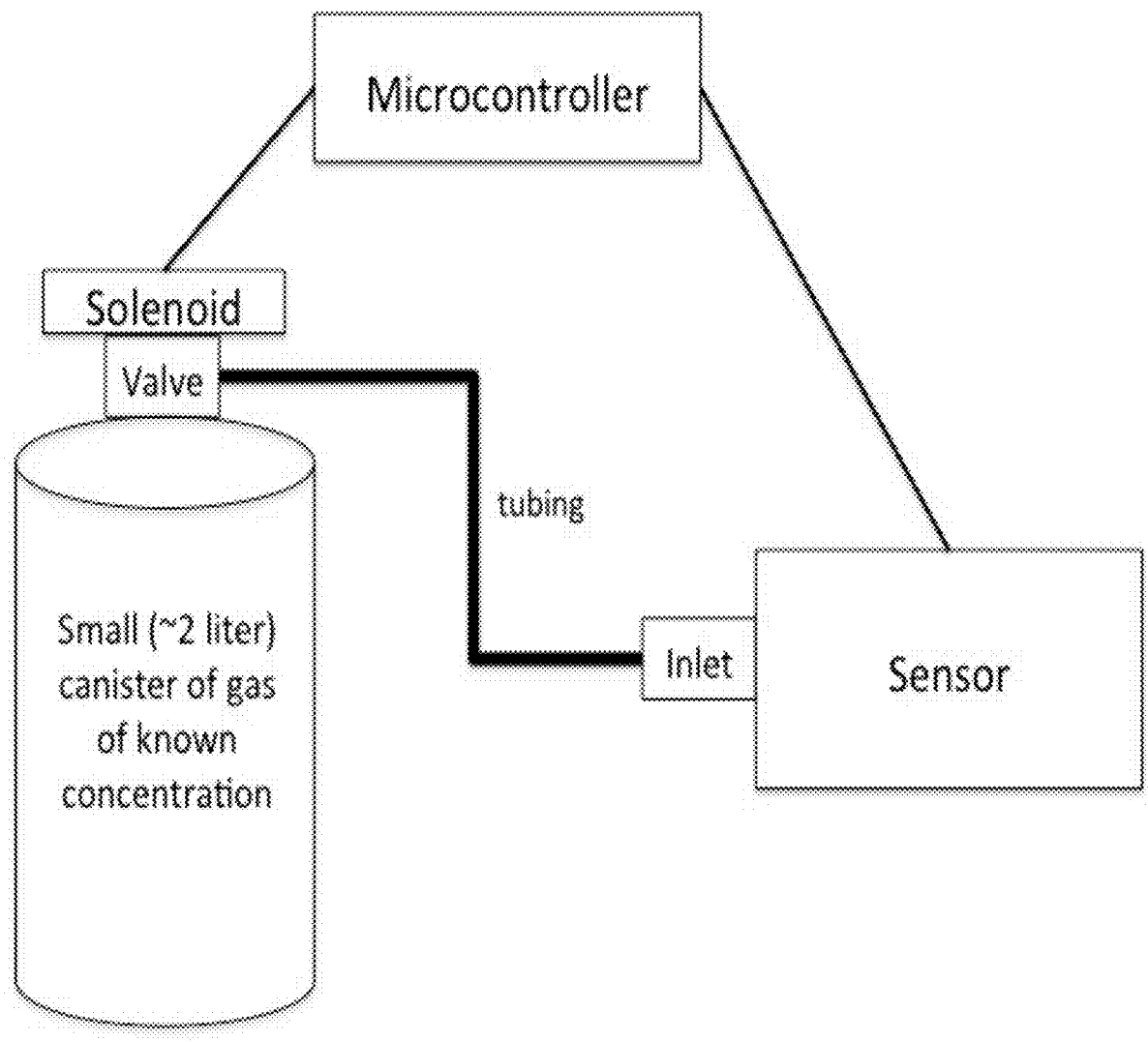
FIG. 8 is a schematic diagram illustrating an example field calibration system.

A common problem in many low- and moderately-priced analyzers is zero drift, where the sensitivity remains consistent but the baseline or zero point drifts with time or environmental conditions. As shown in FIG. 8, a low-cost efficient method is provided here using a small canister of air with known gas concentration. This air can be low-cost breathing air. The canister is taken into the field periodically as needed. This air is allowed to run smoothly into the K30 sensor using an inlet nibble for a few minutes. Using the sensor measured values and the known concentration, the sensor is then adjusted for drift either on board or remotely on the server data processing side, resulting in greatly improved stability and detection limit. Alternatively, the procedure can be automated using a solenoid valve that is controlled by software to periodically run the zero-drift correction as above, with a canister or air tank stay at each site.

1.5 Co-Locate with Standard Monitoring Stations

Government agencies such as the US Environmental Protection Agency (EPA), the Ministry of Environmental Protection of China (MEP), the European Environment Agency (EEA), their regional counterparts, and many scientific and educational institutions run standard air monitoring stations. Some of the low-cost sensors in a dense network can be co-located at such stations for calibration. For example, for urban greenhouse gas monitoring, the US National Institute for Standards and Technology (NIST) has installed ~10 high accuracy Picarro $CO_2/CH_4$ analyzers both in the City of Indianapolis and in the Baltimore-Washington Metropolitan Region. The majority of the sensors will be at locations that lack a Picarro. All of the K30s will be handled in an identical manner. The co-location of a subset of the K30 sensors with sites that include a Picarro that can provide a ground truth for the low-cost network.

1.6 Network-Enabled Calibration

Figure 9:
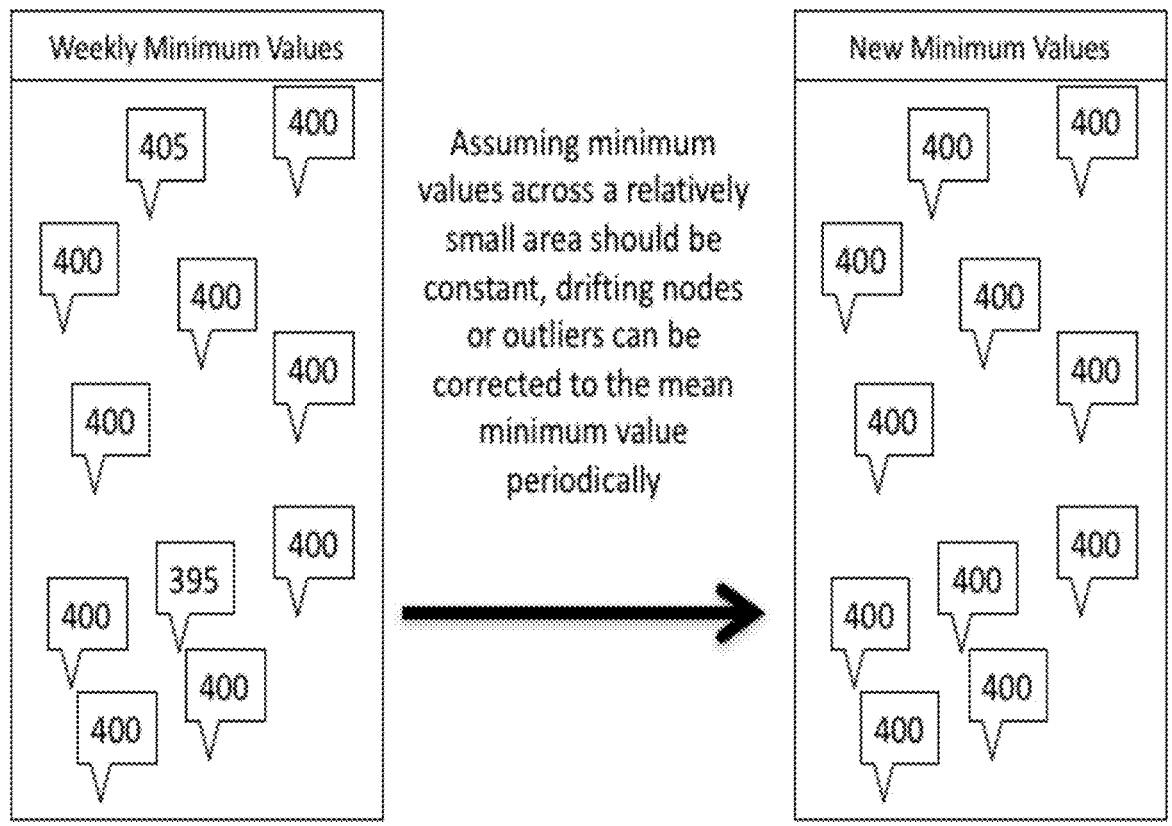
FIG. 9 illustrates a spatial zero correction concept based on statistical methods according to some embodiments.

Because the atmospheric $CO_2$ and other gases behave in a predictable way, the spatial and temporal characteristics can be utilized to calibrate a network of sensors for potential zero-drift. In one approach, the background concentration in a region network can be determined using the lowest value over a period of time using the co-located high-accuracy sensors. This value can then be used as a calibration target for zero-drift adjustment for other sensors. In a more sophisticated approach, the data assimilation according to some embodiments will incorporate the full network data, together with meteorological variables to create a 4-dimensional view of $CO_2$. It can also be used to reject bad measurements that are not internally consistent and to calibrate individual sensors in the network. FIG. 9 is a description of a spatial zero correction concept based on statistical methods, where the scale of the area can be, for example, a neighborhood, a sub-city region, a metro city, a province or state, etc.

Once a calibration procedure is established, it will be implemented as an algorithm as part of the standard data processing package, but each sensor will have its own set of parameter values. These algorithms will be refined as more data are collected and knowledge on these sensors improves, and the parameter values will be updated remotely as needed. According to some embodiments, a self-learning process can be employed to update the parameter values and continuously calibrate the sensors. Such a self-learning process can be based on, for example, artificial intelligence (AI), cloud computing, big data collection and analysis, etc.

The networked monitoring system can include a processor, such as a computer or a server, which communicates with the plurality of distributed sensors. In some embodiments, the server can communicate with the plurality of distributed sensors directly, using communication methods known to those of ordinary skill in the art. The server can receive data from the sensors, calibrate the data using the algorithms described above, and send instructions to the sensors.

In some other embodiments, the network can be layered. For example, the server can communicate with one or more base stations through a relatively long distance, using cellular network, local area network, or other communication means. The base station can include a long-range communication module configured to communicate with the server. The base station can also communicate with a plurality of satellite modules or sensors at a shorter range. The base station itself can of course also include sensors similar or complementary to those sensors of the satellite modules. In some embodiments, the base station also obtains environmental data such as temperature, pressure, humidity, etc., to calibrate the data obtained by the sensors.

2. Instrumentation: Hardware and Software 2.1 Hardware 2.1.1 Model 0

Figure 10:
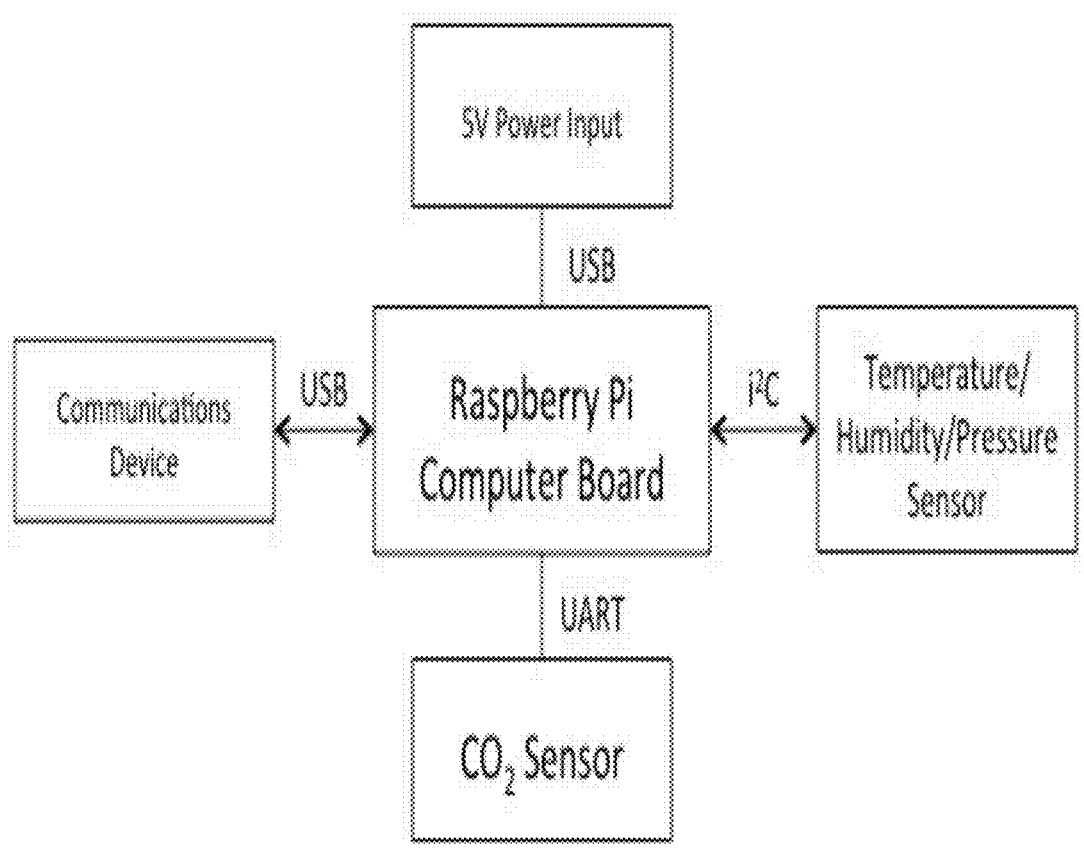
FIG. 10 is a schematic diagram of a Raspberry-Pi-based system according to some embodiments.

Some embodiments disclosed herein can be described with respect to prototyping/lab models, but are not limited to these models. An example system comprises the Raspberry Pi mini-computer (acting as the data logger, processor and data transmitter) and various sensors plugged in directly to the GPIO header pins of the Pi or through a breadboard, with ADC (Analog-to-Digital Converter) as needed (FIG. 10 top-left). Raspberry Pi is an open source electronics/computing platform using a full Linux operating system that supports most hardware found in a laptop computer, including Wi-Fi and Ethernet. In some embodiments, an Arduino-based system can be employed. In some example embodiments described below, Raspberry Pi is selected for its versatility and ease to handle both low-level (such as data collection) and high-level (such as data transmission) functionalities. Software for data connection and initial data processing has been written and tested for each sensor. Various versions of this model have been used over the last two years in the UMD Environmental Monitoring Lab rooftop station. This version of the device can be connected to the Internet either through Wi-Fi using a USB adapter, a hard-wired Ethernet connection, over a 3G cellular network using a USB modem, or other communications methods known in the art. The latest version (beta version) is being installed in an experimental mini-network.

2.1.2 Model A

Figure 11:
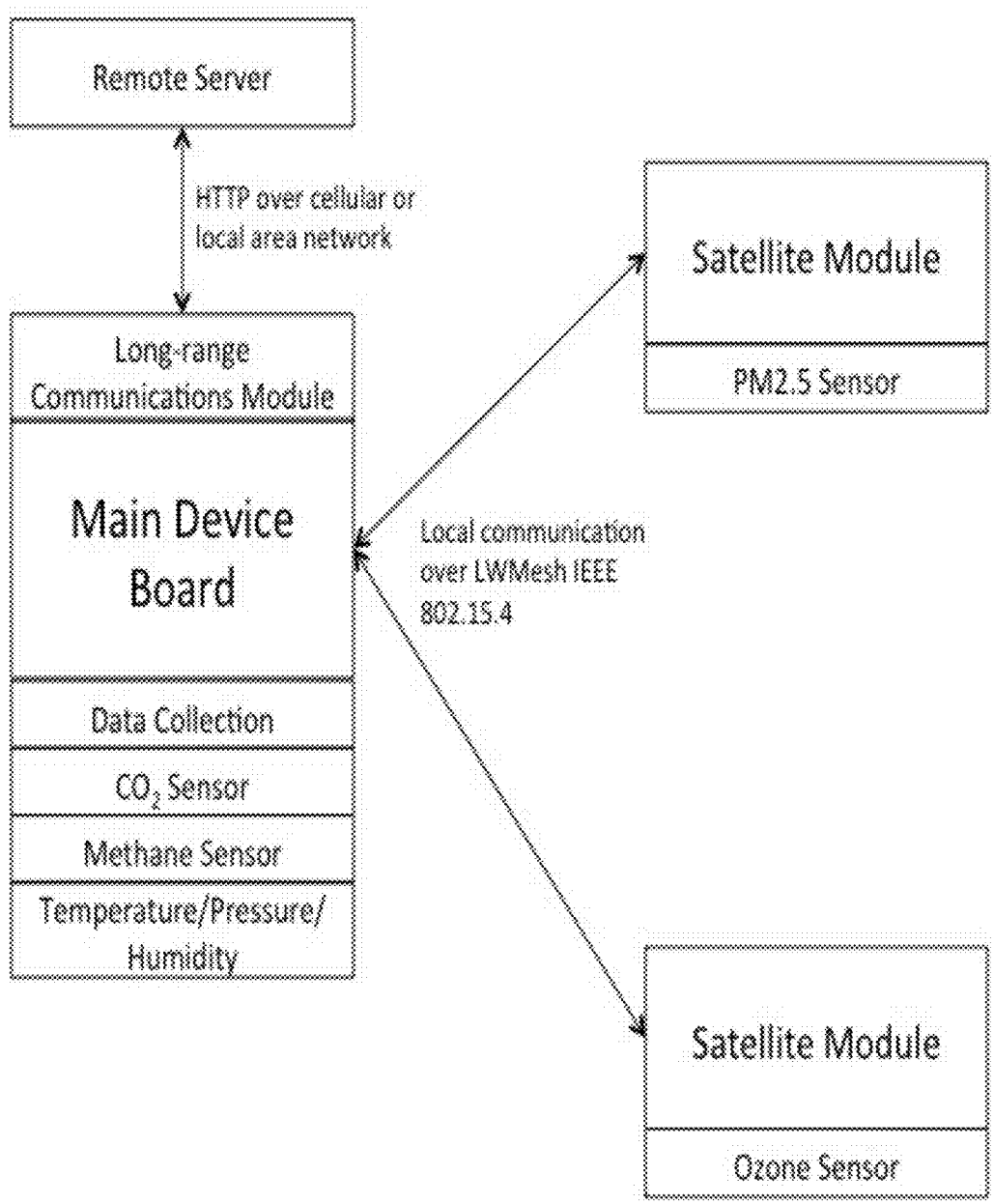
FIG. 11 is a schematic diagram of a custom built base station and satellite system according to some embodiments.

Model A is a base station comprising a main board with sensors for 5 example "basic" variables: temperature, humidity, air pressure, $CO_2$ and $CH_4$. The main board, developed in house featuring an Atmel ATmega644 microcontroller, serves the function of managing the 5 basic sensors (above), communicating with the satellite modules (below), long-range communication through a connector for a interchangeable communications board (allowing for Ethernet, cellular, or WiFi depending on need), as well as power regulation for solar or AC plugin. Various components are shown in FIG. 11.

2.1.2.1 Power Consumption

Power consumption of a lab-model tested is approximately 900 mA at 5 V, similar to the power consumption of a small clock radio, with the largest draw by Raspberry Pi. This level of energy consumption is higher than some ultra-low power system such as Waspmote, but the sensors collect data at much higher frequency (every 2 seconds) and accomplish many more tasks. The model-A design disclosed herein has a power-consumption of 100 mA at 5V. The power can be supplied by a <10 W solar panel with a Li-ion battery backup that provides sufficient power in the event of a succession of overcast days.

2.1.3 Satellite Modules

"Satellite" modules can comprise simple electronics board that hosts sensors of flexible combination/choices and transmits data to the base station. One or more "satellite" modules can be connected wirelessly to the "base station" (Model-A main module) over an IEEE® 802.15.4 lightweight mesh network, allowing freedom in choosing the combination of sensors tailored to individual site and specific application, as well as additional 'bare-bone' $CO_2$ sensor(s) without the full package for data transmission etc. On the satellite modules, sensors for O3, CO, SO2, NO2 from Alphasense can be employed.

2.1.4 Weather Shield

Figure 12:
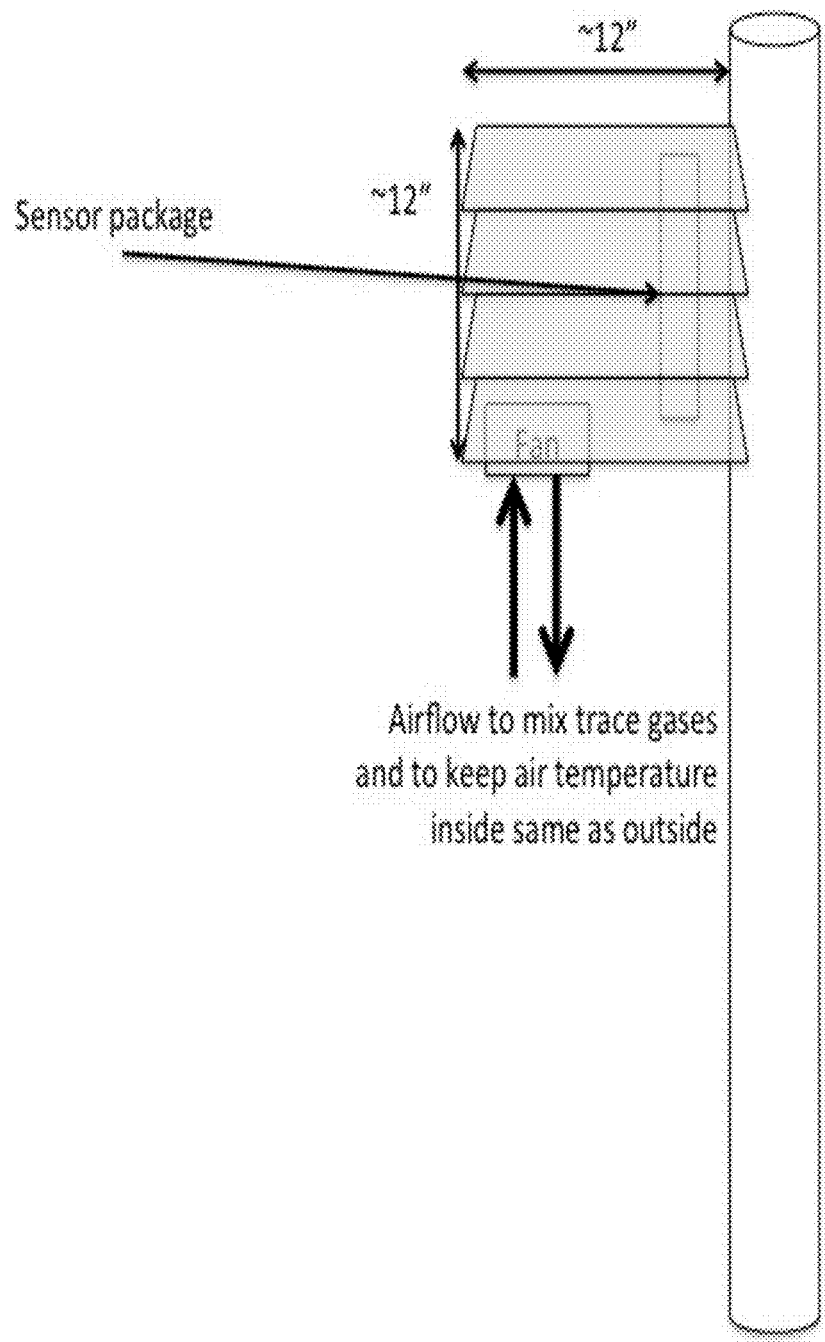
FIG. 12 is a schematic of an example weather shield.

As shown in FIG. 12, a weather shield can be a modified version of a weather station enclosure (a.k.a. Stevenson Screen) as used by World Meteorological Organization (WMO) for Automatic Weather Stations (AWS). It can be specifically designed for dense urban environmental monitoring needs with the following considerations: (1) it can be significantly cheaper and smaller than the WMO standard; (2) it can allow more air circulation than a typical radiation shield, which may be too small and too tight for a sensor package; (3) it can minimize the difference between the environmental variables measured inside and outside. Additionally, a low power-consumption fan will help with ventilation, particularly useful during hot and windless weather conditions.

2.2 Software

The main device board features a connection for a long-range communication module. Depending on usage case, the module can be based off of Wi-Fi, Ethernet, or GSM cellular. Each module uses a communications controller that interfaces with the Atmel microprocessor over a serial connection and the software is written such that they can be interchangeable. Data is transmitted over HTTP using one of these modules on a pre-determined basis, and software for the Atmel microprocessor can be updated from a repository on a remote server.

In some embodiments, the environmental monitoring system is a smart and autonomous system. The low-cost sensor 'Internet of Things' approach allows for a network with a high density of nodes, but if they are not self-sufficient, the cost of maintenance of the network would rapidly make implementation unfeasible. Data collection is automated on a regular schedule and configurable. Since the devices are constantly connected to the Internet through either Wi-Fi, cellular, or Ethernet, they will also automatically upload data, and diagnostic information to a centralized server and data repository. Additionally, this constant connection will also check the repository for software updates and parameter settings, to change features such as data collection frequency remotely without physically interacting with the device. The expectation of constant communication permits a system administrator to quickly see if a node requires service, either because of a diagnostic message, or because of a loss of communication.

In addition to using the environmental monitoring system in a connected observation network, there are other applications that can employ the hardware. By including a GPS receiver, the already low-cost, low-power, small, and autonomous apparatus can be mounted on vehicles for making observations that vary in space. Nodes can be attached to cars, bikes, buses, or railcars, and provide a horizontal profile of atmospheric conditions. Additionally, the notes can be mounted to UAVs or attached to tethered balloons or sondes to perform vertical profiles of the atmosphere. Various nodes or sensors can also be deployed with airplanes such as commercial airliners to obtain a 4D presentation of data. In some embodiments, consumer nodes (sensors) can be developed, paired with smartphone apps, to monitor atmospheric conditions in users backyards. The data can be viewed locally, as well as stored on a server.

Figure 13:
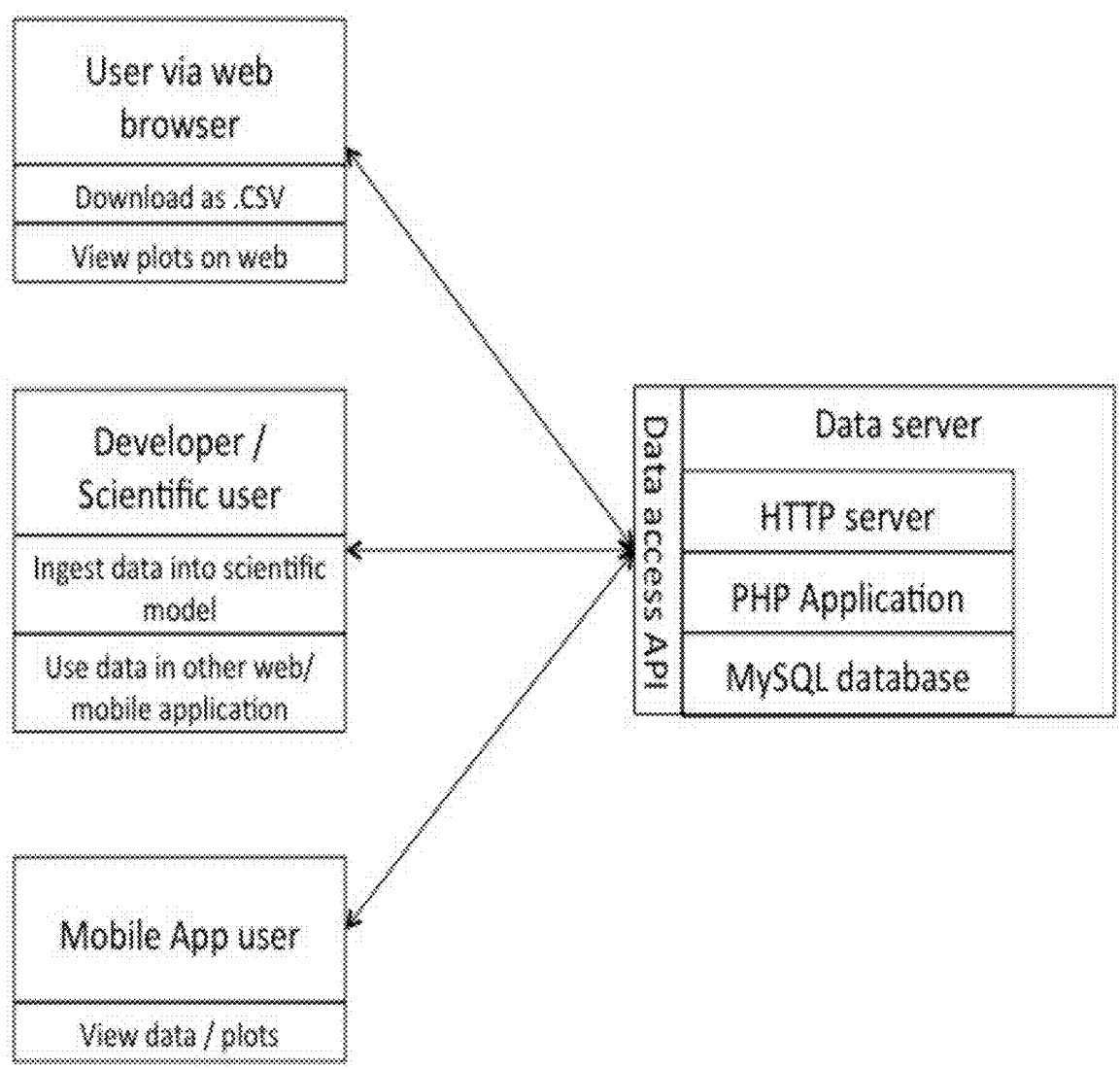
FIG. 13 shows an example of the data API for internal as well as external use.
Figure 14:
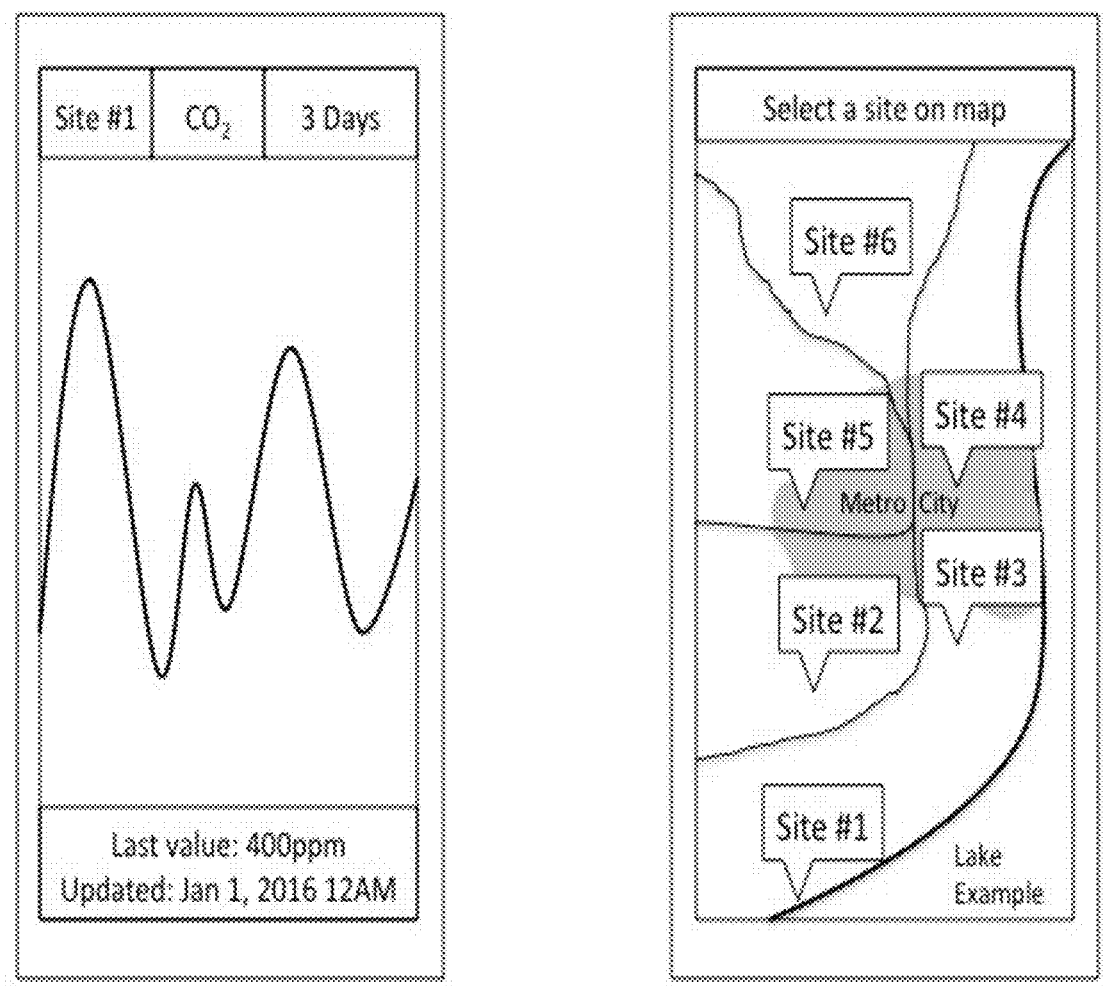
FIG. 14 is a schematic diagram of a custom mobile app for users to view data in near real-time according to some embodiments.

As shown in FIG. 13 and FIG. 14, custom software has been written for the Atmel ATmega644 microcontroller to collect data from the sensors on the device board. The software architecture is asynchronous and interrupt driven, allowing for minimal power consumption and maximizing CPU efficiency. A hardware timer decides when tasks are to be initialized or completed and the software is written so that the processor can do other tasks while waiting on a request, rather than idly waiting for a response. This software controls which sensors are queried and when, as well as the driver interfaces for the on-board communications protocols and the flash storage.

For the local-area lightweight mesh network, the stock Atmel library is used as an example, which can be sufficient for the needs of the environmental monitoring system. For long-range communications, the software depends largely on which method of communication is being used. For cellular networks, AT commands are used over serial to transmit data in HTTP packets. For Wi-Fi and Ethernet, the network controller connects to a local area network, and then the data is sent over HTTP. Each of the long-range connections are also used to periodically check for firmware updates as well as updates to parameters stored in the device's memory.

Located on a centralized server is a repository of software for the Atmel microprocessor. Developers modify and update the system software and place it in this repository, and a remote device board will check periodically to see if it needs to download and install updated software. In addition to the main system software, a database of parameters including but not limited to data upload frequency, the list of variables to collect, even the amount of data to store in the on-board memory, is kept for each node in the network. The remote system board will also check periodically to see if it needs to update its stored parameters to match what is specified in the server-side database.

Each remote device board sends its stored data periodically to a server over the Internet using HTTP. On the server-side, a PHP page may be provided. If a HTTP POST is submitted to the page, the data can be transmitted to the server, and inserted into a MySQL database stored on the server. These data are archived in this database as raw original data and backed up on another storage device.

The raw original data stored in the MySQL database is processed both for quality control and for time averaging, and is then stored in another database for archival and usage. The original data is first checked for obvious errors or missing data, which is flagged, and then averaging of various intervals is applied. This creates datasets with varying temporal resolution for different applications.

An API has been written to access the data stored in the MySQL database through the web. There is a webpage for users to log in, visualize and download data as a plain text or comma-separated (CSV) file. There also is software written for the server backend to output data from the MySQL database as a binary or text file for use in scientific applications. Additionally, there is a PHP page that returns a JSON table of data for a given query of data type, sensor, node identification, and time period.

An Android app has been developed (and an iOS port is in the works) that sends requests to this PHP API page and parses the JSON for a user to visualize the data at their nearest location as well as at any other locations the administrator has allowed for their user account.

In some embodiments, plug-and-play low-cost sensors are provided, for example, to users for plug-in or wirelessly connected to the users' smart phones, computers, automobiles, drones, home appliances, etc. The sensors can also be provided to airlines, car rental companies, transportations companies, etc., and be associated with airplanes, cars, trucks, ships, etc. A network of distributed sensors can therefore be established, and the sensors can provide measured environmental data through a variety of communication channels, to one or more processing centers.

The sensors can be provided to the users at no cost, or for purchases. The app can provide initial process of the data collected, and provide feedback to the users, such as information processed and assimilated by the processing centers.

In some embodiments, such a network of distributed sensors can cover ground, air, water (such as the ocean by ships), and space (e.g., by satellites).

3. Computational Data Assimilation System to Invert Fluxes at High Spatiotemporal Resolution A computational tool is provided, which can combine the high-density sensor network data with other additional data including global in-situ network (GLOBALVIEW-CO2, 2013: Cooperative Global Atmospheric Data Integration Project. 2013, updated annually. Multi-laboratory compilation of synchronized and gap-filled atmospheric carbon dioxide records for the period 1979-2012 (obspack_co2_1_GLOBALVIEWCO2_2013_v1.0.4_2013-12-23), compiled by NOAA Global Monitoring Division: Boulder, Colo., U.S.A) and satellite observations from such as the Orbiting Carbon Observatory OCO-2 (Crisp, D., Fisher, B. M., O'Dell, C., Frankenberg, C., Basilio, R., Bosch, H., Brown, L. R., Castano, R., Connor, B., Deutscher, N. M., Eldering, A., Griffith, D., Gunson, M., Kuze, A., Mandrake, L., McDuffie, J., Messerschmidt, J., Miller, C. E., Morino, I., Natraj, V., Notholt, J., O'Brien, D. M., Oyafuso, F., Polonsky, I., Robinson, J., Salawitch, R., Sherlock, V., Smyth, M., Suto, H., Taylor, T. E., Thompson, D. R., Wennberg, P. O., Wunch, D., and Yung, Y. L.: The ACOS CO2 retrieval algorithm—Part II: Global XCO2 data characterization, Atmos. Meas. Tech., 5, 687-707, doi: 10.5194/amt-5-687-2012, 2012). The system uses an Ensemble Transform Kalman Filter (Hunt, B. R., E. Kostelich, and I. Szunyogh (2007), Efficient Data Assimilation for Spatiotemporal Chaos: a Local Ensemble Transform Kalman Filter, Physica D, 230, 112-126) that combines the best of prior knowledge and model estimates with anticipated high accuracy observations, taking into account the uncertainty in both. The algorithm can be as following.

Its inputs are the observations $y^o$, the ensemble forecast $$x_k^b(t)=M(x_k^b(t-1))$$

with mean $\bar{x}^b$, and the forecast of the observation $$y_k^b=h(x_k^b)$$

where M represents the full nonlinear model, k is the index for model ensemble member, h is an 'observation operator' that 'maps' model prediction onto observation space in order to compute the observation model error covariance $y^o-h(x_k^b)$. This is an ensemble square-root filter in which the observations are assimilated to update only the ensemble mean while the ensemble perturbations $x_k^b-\bar{x}^b$ are updated by transforming the forecast perturbations through a transform matrix:

$$\bar{x}^a=\bar{x}^b+X^b\tilde{P}^a(HX^b)^TR^{-1}[y^o-h(\bar{x}^b)]$$

$$X^a=X^b[(K-1)\tilde{P}^a]^{1/2}.$$

Here K is the total number of ensemble members, $X^a$, $X^b$ are perturbation matrices whose columns are the analysis and forecast ensemble perturbations, respectively. $X^b$ is updated every analysis time step, therefore the forecast error covariance $$P^b = \frac{1}{K-1}X^b X^{bT}$$

is flow-dependent. $\tilde{P}^a$, the analysis error covariance in ensemble space, is given by $$\tilde{P}^a=[(K-1)I+(HX^b)^TR^{-1}(HX^b)]^{-1},$$

which has dimension K by K, much smaller than both the dimension of the model and the number of observations. Thus, the algorithm performs the matrix inverse in the space spanned by the forecast ensemble members, which greatly reduces the computational cost.

Specific implementations can involve several advanced techniques, including the following examples.

Vertical localization of column mixed $CO_2$ observations: Since the time scales for changes in the atmospheric $CO_2$ are much shorter near the surface than in the upper troposphere, a vertical localization can be created for the column average changes that was larger near the surface. The larger attribution of column total $CO_2$ changes to the layers near the surface resulted in a significant increase in the accuracy of the analysis of carbon fluxes.

Four-dimensional (4D) assimilation, where the 4th dimension refers to time, which 'matches' any observation at the exact time the data was collected with corresponding model forecast for calculating the covariance. The multiple data-model pairs accumulated since the previous assimilation step are then assimilated at the next assimilation step, allowing a flexible assimilation window without sacrificing temporal information.

Use of a short assimilation window (1 hour or shorter for regional). This contrasts with many current inversion systems with much longer window lengths (weeks to months). It takes advantage of a new generation of data provided by satellite, continuous monitoring at tall towers, aircraft and field campaigns especially over continental regions where both fossil fuel emissions and natural sources and sinks have high spatial and temporal variability. Short time windows also minimize effects of non-linearity on the ensemble Kalman filter's linearity assumption, as rapidly evolving weather systems are now resolved.

A temporal smoother that allows the use of data over a time span longer than the assimilation window with temporal weighting such that the further away from the current time step, the less the contribution. This accommodates the apparent competing needs of a short assimilation window and the low temporal resolution of certain data such as flask sampling.

A time filter that combines the inverted fluxes from previous several steps of data assimilation analysis as a weighted average. The resulting mean is used in the next assimilation step as prior for the forward model transport. This has the effect to smooth out the noise in time, especially when data is sparse within assimilation window, and improves the system's stability.

While the system has a number of unique characteristics, the above are particularly relevant here as they enable (1) resolving the vertical contribution (via model prior) to satellite column $CO_2$, (2) allowing the intermittently overlap satellite and ground observations to co-constrain the model at very high spatial and temporal resolution of the original data, extracting potential high-frequency signal from a noisy background while retaining the low-frequency and large-scale $CO_2$ and flux variations. Obviously, besides data and assimilation techniques, the ability to extract high frequency information will also depend on the representation of atmospheric transport.

Figure 15:
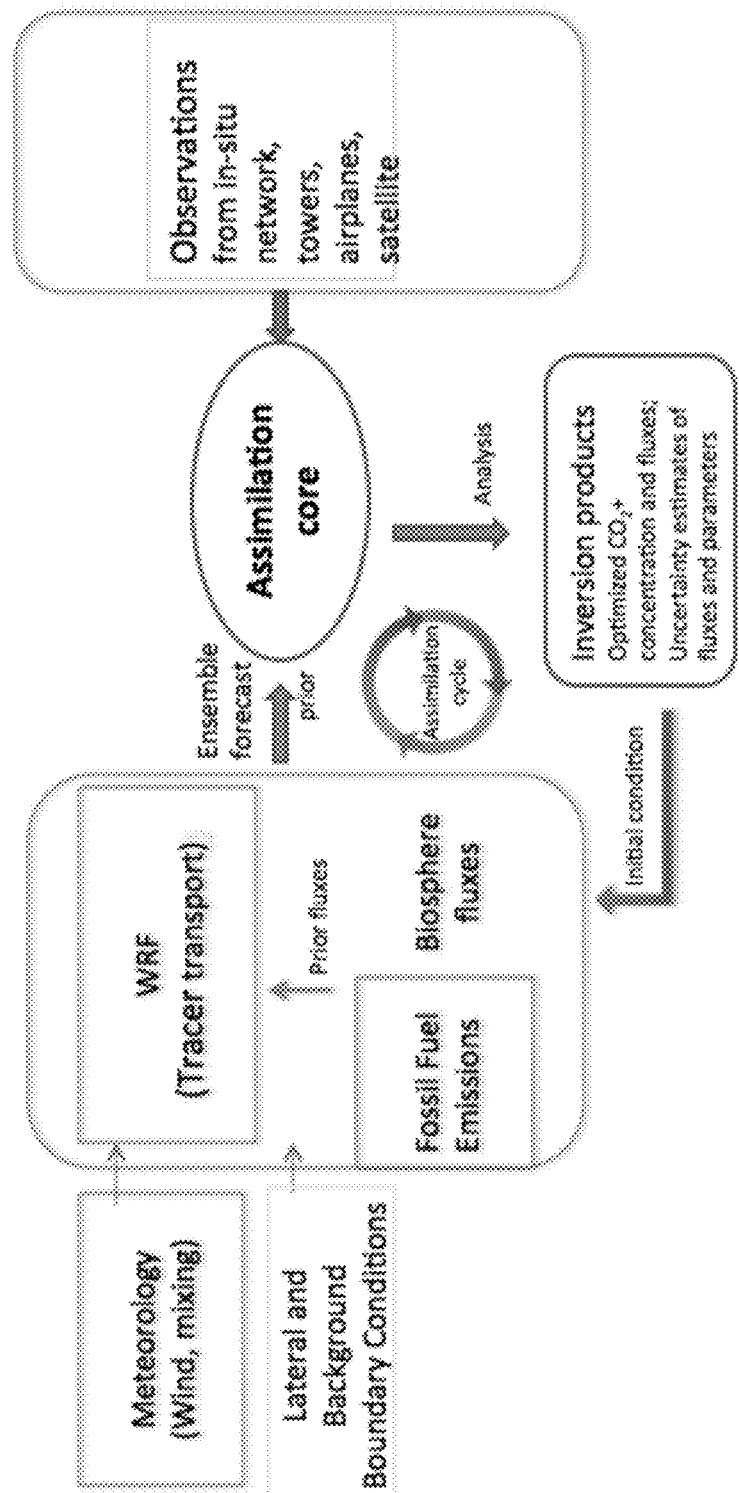
FIG. 15 is a diagram of a coupled ensemble data assimilation system for calculating high spatial-temporal resolution fluxes using data from regional sensor network and other sources according to some embodiments.

An example regional carbon data assimilation system can comprise the following components and steps, as illustrated in FIG. 15.

A global carbon data assimilation system using the same data assimilation core, the GeosChem atmospheric transport model at a typical 2 degrees by 2.5 degrees horizontal resolution with the option for a nested domain at 0.25°× 0.3125° resolution. The data input includes global $CO_2$ network, satellite observations such as GOSAT and OCO-2 and site observations.

A meso-scale atmospheric model WRF at a typical 1 km resolution or less is embedded inside the global model above, which provides boundary conditions. The regional model uses the same data assimilation core, but with high-resolution prior fossil fuel emissions and biospheric fluxes.

Prior estimates of fossil fuel emissions can come from a variety of products, e.g., ODIAC (1 km and monthly resolution; Oda, T. and Maksyutov, S.: A very high-resolution (1 kmx 1 km) global fossil fuel CO2 emission inventory derived using a point source database and satellite observations of nighttime lights, Atmos. Chem. Phys., 11, 543-556, doi:10.5194/acp-11-543-2011, 2011). When available, the regional system can also use street-level prior emissions, for example, as produced in the Hestia project for Indianapolis (Gurney, K. R., I. Razlivanov, Y. Song, Y. Zhou, B. Benes, and M. Abdul-Massih, 2012: Quantification of Fossil Fuel CO2 Emissions on the Building/Street Scale for a Large U.S. City, Environ. Sci. Technol., 46, 12194-12202, doi:10.1021/es3011282).

Prior biospheric fluxes is provided by the VEGAS terrestrial carbon model (Zeng, N., H. F. Qian, E. Munoz, and R. Iacono, 2004: How strong is carbon cycle-climate feedback under global warming? Geophysical Research Letters, 31; Zeng, N., A. Mariotti, and P. Wetzel, 2005: Terrestrial mechanisms of interannual CO2 variability, Global Biogeochem. Cycle, 19, GB1016, doi:10.1029/2004GB002273), driven by observed climate and 30 m land surface classification. VEGAS has been a contributor to the annual global carbon budget (Le Quéré, et al. Global carbon budget 2014, Earth Syst. Sci. Data, 7, 47-85, doi:10.5194/essd-7-47-2015, 2015), and is a participant of the international TRENDY terrestrial carbon model intercomparison project (Sitch, S. et al. Recent trends and drivers of regional sources and sinks of carbon dioxide. Biogeosciences 12, 653-679 (2015)) and the North American Carbon Program MsTMIP project (Huntzinger, D. N., Schwalm, C., Michalak, A. M., Schaefer, K., King, A. W., Wei, Y., Jacobson, A., Liu, S., Cook, R. B., Post, W. M., Berthier, G., Hayes, D., Huang, M., Ito, A., Lei, H., Lu, C., Mao, J., Peng, C. H., Peng, S., Poulter, B., Riccuito, D., Shi, X., Tian, H., Wang, W., Zeng, N., Zhao, F., and Zhu, Q.: The North American Carbon Program Multi-Scale Synthesis and Terrestrial Model Intercomparison Project Part 1: Overview and experimental design, 2013, Geosci. Model Dev., 6, 2121-2133, 10.5194/gmd-6-2121-2013).

VEGAS is currently running in near real time (1-month delay) with observed climate forcing in a TRENDY-like fashion. One version of VEGAS model (VEGAS2.3-diurnal) runs at hourly time step, thus resolving diurnal cycle of photosynthesis and respiration mechanistically, an improvement from a popular approach by downscaling monthly flux (Olsen, S. C., and J. T. Randerson (2004), Differences between surface and column atmospheric CO2 and implications for carbon cycle research, J. Geophys. Res., 109, D02301, doi:10.1029/2003JD003968).

The prior fluxes and large-scale boundary conditions are fed to the WRF-Chem model, and then transported using the WRF meteorological wind fields. The data assimilator will combine all these and return optimized surface fluxes and GHG concentrations, together with uncertainty quantification.

An aspect is how the temporal information is used, as different data overlap only intermittently in space and time. A 4D-LETKF (above) can be employed to handle this. For example, a 1-hour assimilation window can be used, within which co-variance between 1-minute data from ground sensors (NIST Picarro and low-cost) will be calculated from WRF-Chem $CO_2$ forecast ("background" in DA terminology) at the exact corresponding time. These co-variances, via observational operator, will be used for assimilation at each hour.

To use satellite OCO-2 data, for example, two different options can be run: 1) Averaging to hourly or less (assimilation window) and model grid-like resolution; 2) Using individual OCO-2 measurements (soundings') at its highest resolution (footprint of ~3 km$^2$).

While a DA system according to some embodiments disclosed herein handles either straightforwardly, each has its pros and cons depending on signal-noise ratio in OCO-2 data: averaging will reduce noise but at the cost of losing high-resolution information. In a way, the DA system will push the data to its limit of utility. When combined with the in-situ network, it offers hope to identify even some localized and transient emission sources.

The above system will provide best-estimate fluxes and 3D $CO_2$ fields, together with the ensemble-base uncertainty estimate.

The data can be then made available in graphic and electronic format to users via websites and smartphone apps. The raw data can be quality controlled and calibrated to form Level-1 data (i.e., calibrated surface $CO_2$ mixing ratio). The inversion system will provide a Level-2 product of model-data fused fluxes at 1-4 km (standard) and 500 m (special cases) resolution and hourly frequency. The ensemble system also provides uncertainties resulting from $CO_2$ data error and atmospheric transport error.

The data can be further processed into various Level-3 products, including temporally (monthly and annual) and spatially aggregated carbon flux at 1-4 km spatial resolution, as well as for county/city/district or other administrative regions, thus offering atmospheric "top-down" emissions estimates independent of the inventory data normally used by local governments (e.g., DDOE, 2013; Kennedy, C., J. Steinberger, B. Gasson, Y. Hansen, T. Hillman, M. Havranek, D. Pataki, A. Phdungsilp, A. Ramaswami, and G. V. Mendez (2010), Greenhouse gas emissions from global cities, Environ. Sci. Technol., 43(19), 7297-7309). The localized data contain more tangible information on patterns and causes of regional carbon emissions, providing more immediate feedback to emissions reduction effort. It can facilitate actions by governments, organizations, and individuals.

As will be appreciated by those of ordinary skill in the art, the present disclosure may be embodied as a method, a system, an apparatus, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium (e.g., non-transitory computer readable medium) having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object-oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet.

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general-purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer (e.g., computing device 12) or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

All references referred to in the present disclosure are incorporated by reference in their entirety. Although specific embodiments have been described above in detail, the description is merely for purposes of illustration. It should be appreciated, therefore, that many aspects described above are not intended as required or essential elements unless explicitly stated otherwise. Various modifications of, and equivalent acts corresponding to, the disclosed aspects of the exemplary embodiments, in addition to those described above, can be made by a person of ordinary skill in the art, having the benefit of the present disclosure, without departing from the spirit and scope of the disclosure defined in the following claims, the scope of which is to be accorded the broadest interpretation so as to encompass such modifications and equivalent structures.

The invention claimed is:

1. An environment monitoring method, comprising:
obtaining environmental information by combining a plurality of observations based on a plurality of sensors;
wherein the plurality of sensors include a first set of sensors each of a first accuracy at a first cost, and a second set of sensors each of a second accuracy at a second cost, the second accuracy being higher than the first accuracy, and the second cost being higher than the first cost, and
wherein the first set of sensors form a network comprising a plurality of distributed sensors at a first density;
the method further comprising:
obtaining environmental data with the plurality of distributed sensors, wherein the plurality of distributed sensors are calibrated to achieve a third accuracy suitable for environmental monitoring, and wherein the third accuracy is higher than the first accuracy;
assimilating the obtained environmental data together with meteorological information to derive information on the environment with a first resolution higher than a second resolution of information obtained with a network at a density lower than the first density;
calibrating the obtained environmental data by environmental correction through a successive regressing by solving:

$$y = a_0 x_0 + a_1 x_1 + a_2 x_2 + \ldots a_n x_n + b + \varepsilon_n$$

wherein y represents reported $CO_2$ value from the low-cost sensors, $x_0$ represents true $CO_2$ value, $x_1, x_2, \ldots, x_n$ represent a number of other factors such as air pressure, temperature and humidity respectively;
the residuals $\varepsilon_{n-1}$ and $\varepsilon_n$ at two successive regression steps are related to environmental variables using linear regression successively as:

$$\varepsilon_{n-1} = \varepsilon_n - a_n x_n - b_n,$$

wherein n=1,3 for each environmental variable pressure p, temperature T, and water vapor q, wherein the linear regression method leads to eight correction coefficients, of the form $a_n$ and $b_n$, the method further comprising:
applying the correction coefficients to the equation of y along with the environmental variables to correct sensor CO2 observations for environmental influences:

$$y^* = \{y - b_0 - (a_1 x_1 + b_1) \ldots - (a_n x_n + b_n)\}/a_0;$$

and
displaying the derived information on the environment on a display screen.

2. The method of claim 1, wherein second set of sensors are configured for direct measurement and calibrating the first set of sensors; and
at least some of the plurality of distributed sensors are co-located with standard monitoring stations.

3. The method of claim 1, further comprising an in-situ zero-drift correction.

4. The method of claim 1, further comprising a network-enabled calibration.

5. An environment monitoring method, comprising:
obtaining environmental information by combining a plurality of observations based on a plurality of sensors;
wherein the plurality of sensors include a first set of sensors each of a first accuracy at a first cost, and a second set of sensors each of a second accuracy at a second cost, the second accuracy being higher than the first accuracy, and the second cost being higher than the first cost, and
wherein the first set of sensors form a network comprising a plurality of distributed sensors at a first density;
the method further comprising:
obtaining environmental data with the plurality of distributed sensors, wherein the plurality of distributed sensors are calibrated to achieve a third accuracy suitable for environmental monitoring, and wherein the third accuracy is higher than the first accuracy;
assimilating the obtained environmental data together with meteorological information to derive information on the environment with a first resolution higher than a second resolution of information obtained with a network at a density lower than the first density; and
a computational data assimilation to invert fluxes at a third spatiotemporal resolution to combine measured gas concentrations and meteorological information to derive information on pollution sources and sinks at the first resolution, including:
obtaining inputs from observations $y^o$, the ensemble forecast $$x_k^b(t) = M(x_k^a(t-1))$$

with mean $\bar{x}^b$ and forecast of the observation $$y_k^b = h(x_k^b),$$

wherein M represents a full nonlinear model, k is an index for model ensemble member, h is an observation operator mapping model prediction onto observation space to compute observation model error covariance $y^o - h(x_k^b)$;
applying the covariance as an ensemble square-root filter in which observations are assimilated to update only an ensemble mean while ensemble perturbations $x_k^b - \bar{x}^b$ are updated by transforming forecast ensemble perturbations through a transform matrix:

$$\bar{x}^a = \bar{x}^b + X^b \tilde{P}^a (HX^b)^T R^{-1} [y^o - h(\bar{x}^b)]$$

$$X^a = X^b [(K-1)\tilde{P}^a]^{1/2},$$

wherein K is total number of ensemble members, $X^a, X^b$ are perturbation matrices whose columns are analysis and the forecast ensemble perturbations, respectively. $X^b$ is updated every analysis time step, therefore forecast error covariance $$P^b = \frac{1}{K-1} X^b X^{bT} \quad\quad 5$$

is flow-dependent;
$\tilde{P}^a$, an analysis error covariance in ensemble space, is given by $$\tilde{P}^a = [(K-1)I + (HX^b)^T R^{-1}(HX^b)]^{-1}$$

which has dimension K by K, smaller than both dimension of the full non-linear model and number of observations; thereby performing matrix inverse in the ensemble space spanned by forecast ensemble members, the reducing computational cost;
the method further comprising displaying the derived information on the environment over a map on a display screen.

6. The method of claim 5, further comprising a vertical localization of column mixed $CO_2$ observations.

7. The method of claim 5, further comprising a 4D assimilation.

8. The method of claim 5, further comprising applying a short assimilation window.

9. The method of claim 5, further comprising a temporal smoother.

10. The method of claim 5, further comprising a time filter that combines inverted fluxes from previous several steps of data assimilation analysis as a weighted average.

11. An environment monitoring system, comprising:
a plurality of distributed sensors at a first density configured to obtain environmental data, wherein the plurality of distributed sensors comprise a first set of sensors each of a first accuracy at a first cost, and are calibrated to achieve a third accuracy higher than the first accuracy and suitable for environmental monitoring; and
one or more processing circuits configured to assimilate the obtained environmental data together with meteorological information to derive information on the environment with a first resolution higher than a second resolution of information obtained with a network at a density lower than the first density;
wherein the plurality of sensors include a first set of sensors each of a first accuracy at a first cost, and a second set of sensors each of a second accuracy at a second cost, the second accuracy being higher than the first accuracy, and the second cost being higher than the first cost;
the one or more processing circuits are further configured to:
obtain environmental data with the plurality of distributed sensors, wherein the plurality of distributed sensors are calibrated to achieve a third accuracy suitable for environmental monitoring, and wherein the third accuracy is higher than the first accuracy; and
calibrate the obtained environmental data by environmental correction through a multivariate regression to calculate regression coefficients for each of a plurality of K30 sensors to obtain five correction coefficients $a_n$ and $b_n$, wherein n represents each independent variable, for dry $CO_2$ from Los Gatos Fast Greenhouse Gas Analyzers (LGRs), pressure P, temperature T, and water vapor mixing ratio q for an equation:

$$y^* = \{y - b_0 - (a_1 x_1 + b_1) \ldots - (a_n x_n + b_n)\}/a_0$$

along with original K30 data, y, and environmental variables to predict true $CO_2$ concentration observed;
the system further comprising one or more computers to display the true $CO_2$ concentration observed.

12. The system of claim 11, further comprising a base station configured to receive data from at least a subset of the plurality of distributed sensors.

13. The system of claim 11, wherein the one or more processing circuits are further configured to manage the plurality of distributed sensors through at least one of Ethernet, cellular, or Wi-Fi communication channels.

14. The system of claim 11, wherein:
the second set of sensors are configured for direct measurement and calibrating the first set of sensors; and
at least some of the plurality of distributed sensors are co-located with standard monitoring stations.

* * * * *